(12) United States Patent
Muraoka et al.

(10) Patent No.: US 10,309,916 B2
(45) Date of Patent: Jun. 4, 2019

(54) GAS-DETECTING APPARATUS INCLUDING GAS SENSOR AND METHOD OF DETECTING HYDROGEN USING GAS SENSOR

(71) Applicant: Panasonic Intellectual Property Management Co., Ltd., Osaka (JP)

(72) Inventors: Shunsaku Muraoka, Osaka (JP); Satoru Fujii, Osaka (JP); Kazunari Homma, Kyoto (JP); Zhiqiang Wei, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 58 days.

(21) Appl. No.: 15/472,429

(22) Filed: Mar. 29, 2017

(65) Prior Publication Data

US 2017/0307556 A1 Oct. 26, 2017

(30) Foreign Application Priority Data

Apr. 26, 2016 (JP) ................................. 2016-088169

(51) Int. Cl.
*G01N 27/12* (2006.01)
*H01L 45/00* (2006.01)
*G01N 33/00* (2006.01)

(52) U.S. Cl.
CPC ......... *G01N 27/125* (2013.01); *G01N 33/005* (2013.01); *G01N 33/0031* (2013.01);
(Continued)

(58) Field of Classification Search
CPC ............... G01N 27/125; G01N 33/005; G01N 33/0031; H01L 45/146; H01L 45/1233; H01L 45/08
See application file for complete search history.

(56) References Cited

U.S. PATENT DOCUMENTS 4,900,425 A * 2/1990 Sasayama .......... G01N 27/4065
204/406
2002/0187075 A1* 12/2002 Nadanami .......... G01N 27/4074
422/98
(Continued)

FOREIGN PATENT DOCUMENTS

JP 59-058348 4/1984
JP 61-191954 8/1986
(Continued)

OTHER PUBLICATIONS

J. Yu et al., "Hydrogen gas sensing properties of Pt/Ta2O5 Schottky diodes based on Si and SiC substrates", Sensors and Actuators A 172, pp. 9-14, Available online Feb. 25, 2011.
(Continued)

*Primary Examiner* — Huy Q Phan
*Assistant Examiner* — Zannatul Ferdous
(74) *Attorney, Agent, or Firm* — McDermott Will & Emery LLP

(57) ABSTRACT

A gas-detecting apparatus includes a measurement circuit including a gas sensor and a measurement instrument and a decision circuit. Detection cells, included in the gas sensor, each include a first electrode, a second electrode having a surface exposed from an insulation layer, and a metal oxide layer disposed between the first electrode and the second electrode. The resistance values of the detection cells are each allowed to decrease by a contact of gas containing hydrogen atoms with the second electrode. The measurement instrument monitors the resistance values of the detection cells. The decision circuit decides whether the gas is detected or not based on at least one change of the resistance values.

20 Claims, 15 Drawing Sheets

(52) U.S. Cl.
CPC .......... *H01L 45/08* (2013.01); *H01L 45/1233* (2013.01); *H01L 45/146* (2013.01)

(56) References Cited

U.S. PATENT DOCUMENTS

| | | | | |
|---|---|---|---|---|
| 2008/0217174 A1* | 9/2008 | Kanters | .............. | G01N 27/4065 |
| | | | | 204/427 |
| 2010/0025241 A1* | 2/2010 | Hane | .................. | G01N 27/4074 |
| | | | | 204/432 |
| 2013/0000280 A1* | 1/2013 | Korenev | ............ | G01N 15/0656 |
| | | | | 60/276 |
| 2013/0071986 A1* | 3/2013 | Deweerd | ............. | H01L 27/1085 |
| | | | | 438/396 |

FOREIGN PATENT DOCUMENTS

| | | |
|---|---|---|
| JP | 2003-240746 | 8/2003 |
| JP | 2007-278846 | 10/2007 |

OTHER PUBLICATIONS

Song, Junghu et al., "AlGaN/GaN Schottky diode hydrogen sensor performance at high temperatures with different catalytic metals." Solid-State Electronics 49 (2005), pp. 1330-1334.

\* cited by examiner

100

GAS-DETECTING APPARATUS INCLUDING GAS SENSOR AND METHOD OF DETECTING HYDROGEN USING GAS SENSOR

BACKGROUND

1. Technical Field

The present disclosure relates to a gas-detecting apparatus including a gas sensor.

2. Description of the Related Art

Japanese Unexamined Patent Application Publication No. 59-58348 discloses a gas sensor detecting the presence of hydrogen gas as a change in resistance value. This gas sensor includes a tantalum pentoxide ($Ta_2O_5$) material containing palladium (Pd) and glass and includes platinum (Pt) electrodes having the material therebetween.

Sensors and Actuators A, 172 (2011), 9-14 discloses a $Pt/Ta_2O_5$ shot key diode for hydrogen sensing. In the shot key diode, hydrogen molecules are dissociated into hydrogen atoms on the surface of catalytic Pt.

SUMMARY

In one general aspect, the techniques disclosed here feature a gas-detecting apparatus including: a measurement circuit including a gas sensor the includes an insulation film and detection cells covered with the insulation film, and at least one measurement instrument that monitors resistance values of the detection cells; and a decision circuit that decides whether gas containing hydrogen atoms is detected or not based on at least one change in the resistance values. Each of the detection cells includes: a first electrode; a second electrode having a surface exposed from the insulation film; and a metal oxide layer disposed between the first electrode and the second electrode, the metal oxide layer including a bulk area and a local area surrounded by the bulk area, a degree of oxygen deficiency of the local area being higher than that of the bulk area. A reduction in the resistance value of the detection cell is caused by the contact of the gas with the second electrode.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
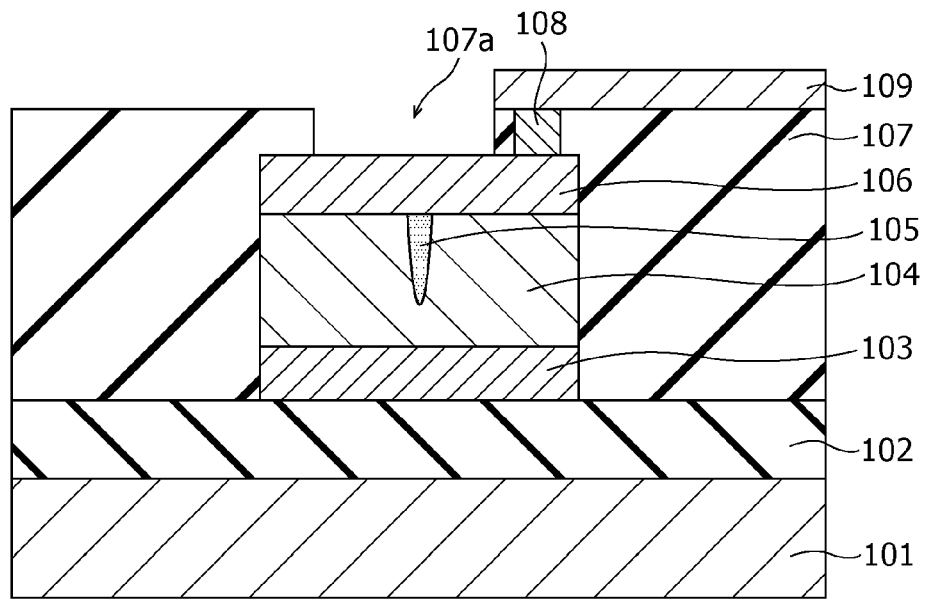
FIG. 1A is a cross-sectional view illustrating an example of a gas detection device according to First Embodiment.

Underlying Knowledge Forming Basis of the Present Disclosure

The present inventors have diligently studied and, as a result, have found that known gas sensors have the following disadvantages.

In known gas sensors, elements detecting gas are heated to 100° C. or more for improving the sensitivity in detection of hydrogen-containing gas. Consequently, the power consumption in known gas sensors is about 100 mW at the lowest. Accordingly, if such a gas sensor is used in the ON-state at all times, a problem of increasing the power consumption is caused.

A gas-detecting apparatus according to an aspect of the present disclosure can stably detect hydrogen-containing gas with high sensitivity and has excellent power-saving properties.

Embodiments of the present disclosure will now be described with reference to the drawings.

In the drawings, elements having the same structures, behaviors, and effects are denoted by the same reference symbols, and duplicate explanations are omitted. The numerical values, materials, compositions, shapes, methods of forming films, connection relationships between components, and other factors described below are all mere examples for specifically describing embodiments of the present disclosure, and the present disclosure is not limited to these examples. Among the components in the following embodiments, the components not described in independent claims showing the highest-order concept will be described as arbitrary components.

First Embodiment

A gas sensor according to First Embodiment includes a plurality of gas detection devices. The plurality of gas detection devices have the same structure and the same size. The gas detection devices each have a metal-insulator-metal (MIM) lamination structure composed of a resistive film (metal oxide layer) and metal films. Each of the gas detection devices can detect hydrogen-containing gas by utilizing self-heating and gas sensitivity of a local area formed in the resistive film without heating with a heater. Herein, the hydrogen-containing gas is a collective term of gases composed of molecules containing hydrogen atoms and can include, for example, hydrogen, methane, and alcohol.

The structure, process of production, and characteristics of one gas detection device will now be first described, and a gas sensor composed of a plurality of the gas detection devices will be then described.

[Structure of Gas Detection Device]

FIG. 1A is a cross-sectional view illustrating an example of the structure of a gas detection device 100 according to First Embodiment.

Figure 1B:
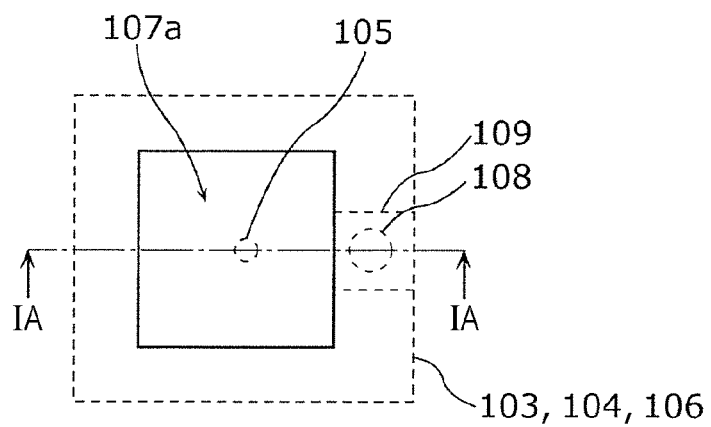
FIG. 1B is a top view illustrating the example of the gas detection device according to First Embodiment.

FIG. 1B is a top view illustrating the example of the structure of the gas detection device 100 according to First Embodiment. The cross-section shown in FIG. 1A corresponds to the cross-section viewed along the cutting line IA-IA of FIG. 1B in the arrow direction.

The gas detection device 100 includes a substrate 101, an insulation film 102 formed on the substrate 101, a first electrode 103 and a second electrode 106 formed above the insulation film 102, a resistive film 104 disposed between the first electrode 103 and the second electrode 106, an insulation film 107, a via 108, and a wiring 109. A main surface of the first electrode 103 and a main surface of the second electrode 106 face each other. The resistive film 104 is disposed so as to be in contact with the main surface of the first electrode 103 and the main surface of the second electrode 106.

The insulation film 107 is provided with an opening 107a for bringing the gas as an object to be detected into contact with the second electrode 106. In other words, the insulation film 107 covers the first electrode 103, the second electrode 106, and the resistive film 104 in such a manner that at least a part of the upper surface (the other surface opposite to the main surface) of the second electrode 106 is exposed without being covered with the insulation film 107.

The resistive film 104 lies between the first electrode 103 and the second electrode 106 and reversibly changes the resistance value based on the electrical signal applied between the first electrode 103 and the second electrode 106. For example, the resistive state of the resistive film 104 reversibly transitions between a high resistive state and a low resistive state depending on the voltage (potential difference) applied between the first electrode 103 and the second electrode 106. The resistive state of the resistive film 104 transitions, for example, from the high resistive state to the low resistive state depending on the hydrogen-containing gas brought into contact with the second electrode 106.

The inside of the resistive film 104 includes a local area 105 being in contact with the second electrode 106 and not being in contact with the first electrode 103. The local area 105 has a degree of oxygen deficiency higher than that of its circumference (i.e., the bulk area of the resistive film 104). The degree of oxygen deficiency of the local area 105 reversibly changes depending on application of an electrical signal between the first electrode 103 and the second electrode 106 and the presence or absence of hydrogen-containing gas in the gas being in contact with the second electrode 106. The local area 105 is a minute region containing a filament (conductive path) consisting of an oxygen defect site.

In the portion of the insulation film 107 covering the upper surface of the second electrode 106, the via 108 passes through the insulation film 107 and is connected to the second electrode 106. The wiring 109 is disposed on the via 108.

In the present disclosure, the "degree of oxygen deficiency" of a metal oxide is a ratio of the amount of the oxygen deficit in the metal oxide to the amount of oxygen in the oxide having a stoichiometric composition consisting of the same elements as those of the metal oxide (herein, the amount of the oxygen deficit is the value obtained by subtracting the amount of oxygen in the metal oxide from the amount of oxygen in the metal oxide having a stoichiometric composition). If the same elements as those of the metal oxide can form a plurality of metal oxides having stoichiometric compositions, the degree of oxygen deficiency of the metal oxide is defined based on one having the highest resistance value among the metal oxides having the stoichiometric compositions. The metal oxide having the stoichiometric composition is more stable and has a higher resistance value compared to metal oxides having other compositions.

For example, if the metal is tantalum (Ta), the oxide having the stoichiometric composition according to the above-described definition is $Ta_2O_5$ and can be expressed as $TaO_{2.5}$. The degree of oxygen deficiency of $TaO_{2.5}$ is 0%, and the degree of oxygen deficiency of $TaO_{1.5}$ is $(2.5-1.5)/2.5$, i.e., 40%. In an oxygen-excess metal oxide, the degree of oxygen deficiency is a negative value. In the present disclosure, the degree of oxygen deficiency can be a positive value, zero, or a negative value, unless otherwise specified.

An oxide having a low degree of oxygen deficiency is more similar to the oxide having the stoichiometric composition and therefore has a high resistance value, while an oxide having a high degree of oxygen deficiency is more similar to the metal constituting the oxide and therefore has a low resistance value.

The "oxygen content" is the rate of the number of oxygen atoms based on the total number of all atoms. For example, the oxygen content of $Ta_2O_5$ is the rate $(O/(Ta+O))$ of the number of oxygen atoms based on the total number of all atoms, i.e., 71.4 atm %. Accordingly, an oxygen-deficient tantalum oxide has an oxygen content higher than 0 atm % and less than 71.4 atm %.

The local area 105 is formed in the resistive film 104 by applying an initial break voltage between the first electrode 103 and the second electrode 106. In other words, the initial break voltage is a voltage applied between the first electrode 103 and the second electrode 106 for forming the local area 105. The absolute value of the initial break voltage may be higher than that of the write-in voltage. The write-in voltage is a voltage applied between the first electrode 103 and the second electrode 106 for causing reversible transition between the high resistive state and the low resistive state of the resistive film 104. Alternatively, the absolute value of the initial break voltage may be less than that of the write-in voltage. In such a case, the initial break voltage may be repeatedly applied or may be continuously applied for a predetermined period of time. As shown in FIG. 1A, application of the initial break voltage forms a local area 105 being in contact with the second electrode 106 and not being in contact with the first electrode 103.

The local area 105 is conceived to contain a filament (conductive path) consisting of an oxygen defect site. The local area 105 has a minute size matching with the filament necessary for current to flow. The formation of the filament in the local area 105 will be described using a percolation model.

The percolation model is based on a theory that a density of oxygen defect sites exceeding a threshold increases the probability of forming a connection of oxygen defect sites in an assumed random distribution of the oxygen defect sites in the local area 105.

In the percolation model, a filament is formed by connection of a plurality of oxygen defect sites in the local area 105. The change in resistance of the resistive film 104 is caused through generation and disappearance of oxygen defect sites in the local area 105.

Herein, the term "oxygen defect" refers to that oxygen in a metal oxide is deficient compared to that of the stoichiometric composition. The term "density of oxygen defect sites" corresponds to the degree of oxygen deficiency. That is, the density of oxygen defect sites increases with the degree of oxygen deficiency.

The local area 105 may be formed at only one region of the resistive film 104 of each gas detection device 100. The number of local areas 105 formed in the resistive film 104 can be determined by, for example, electron beam absorbed current (EBAC) analysis.

If the local area 105 is present in the resistive film 104, the current flowing in the resistive film 104 by application of a voltage between the first electrode 103 and the second electrode 106 is concentrated in the local area 105.

The local area 105 has a small size and therefore generates heat by, for example, a current of about several tens of microamperes flowing at the time of reading out the resistance value. This heat generation causes a considerable increase in the temperature. The power consumption when a current of about several tens of microamperes flows is less than 0.1 mW.

The second electrode 106 is made of a metal (e.g., Pt) having a catalytic action, and the local area 105 is in contact with the second electrode 106. In this structure, the second electrode 106 is heated by the heat generated in the local area 105 to efficiently release hydrogen atoms from hydrogen-containing gas.

If the gas as an object to be tested contains hydrogen-containing gas, hydrogen atoms are released from the hydrogen-containing gas at the second electrode 106, and the released hydrogen atoms bind to oxygen atoms in the local area 105 to reduce the resistance value of the local area 105.

The gas detection device 100 thus has characteristics of decreasing the resistance value between the first electrode 103 and the second electrode 106 by the contact of the second electrode 106 with hydrogen-containing gas. Such characteristics allow the detection of hydrogen-containing gas contained in the gas as an object to be tested by detecting a reduction in the resistance value between the first electrode 103 and the second electrode 106 when the gas is brought into contact with the second electrode 106.

Furthermore, even if the local area 105 is in any of the high resistive state and the low resistive state, the resistance value is decreased by the contact of hydrogen-containing gas with the second electrode 106. Accordingly, the gas detection device 100 can detect hydrogen-containing gas, even if the local area 105 is in any of the high resistive state and the low resistive state. However, in order to more clearly detect a reduction in the resistance value, the local area 105 may be electrically set to a high resistive state, previous to the use of the gas detection device 100.

The details of the gas detection device 100 for obtaining stable resistance change characteristics will now be described.

The resistive film 104 is made of an oxygen-deficient metal oxide. The mother metal of the metal oxide may be at least one selected from transition metals, such as tantalum (Ta), hafnium (Hf), titanium (Ti), zirconium (Zr), niobium (Nb), tungsten (W), nickel (Ni), and iron (Fe); and aluminum (Al). Since transition metals have multiple oxidation states, different resistive states can be achieved by a redox reaction.

Herein, an oxygen-deficient metal oxide has a degree of oxygen deficiency higher than that of a metal oxide having the stoichiometric composition consisting of the same metal elements. The oxygen-deficient metal oxide typically has semiconductor characteristics, while the metal oxide having the stoichiometric composition is typically an insulator. The gas detection device 100 can achieve high reproducibility and stable resistance change behavior by using an oxygen-deficient metal oxide for the resistive film 104.

For example, if the metal oxide constituting the resistive film 104 is hafnium oxide represented by $HfO_x$ in which the value x is 1.6 or more, the resistive film 104 can stably change the resistance value. In such a case, the hafnium oxide film may have a thickness of 3 to 4 nm.

If the metal oxide constituting the resistive film 104 is zirconium oxide represented by $ZrO_x$ in which the value of x is 1.4 or more, the resistive film 104 can stably change the resistance value. In such a case, the zirconium oxide film may have a thickness of 1 to 5 nm.

If the metal oxide constituting the resistive film 104 is tantalum oxide represented by $TaO_x$ in which the value of x is 2.1 or more, the resistive film 104 can stably change the resistance value.

The compositions of the above-mentioned metal oxide layers can be measured by Rutherford backscattering spectrometry.

The materials for the first electrode 103 and the second electrode 106 are selected from, for example, platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), and titanium aluminum nitride (TiAlN).

Specifically, the second electrode 106 is constituted of a material having a catalytic action of releasing hydrogen atoms from gas molecules containing hydrogen atoms, such as platinum (Pt), iridium (Ir), palladium (Pd), and alloys containing at least one thereof. The first electrode 103 may be constituted of a material having a standard electrode potential less than that of the metal constituting the metal oxide, such as tungsten (W), nickel (Ni), tantalum (Ta), titanium (Ti), aluminum (Al), tantalum nitride (TaN), and titanium nitride (TiN). A material having a higher standard electrode potential is more difficult to be oxidized.

The substrate 101 may be any substrate and is, for example, a silicon single crystal substrate or a semiconductor substrate. The resistive film 104 can be formed at a relatively low substrate temperature and can therefore be also formed on, for example, a resin material.

The gas detection device 100 may further include a load element electrically connected to the resistive film 104, such as a fixed resistance, a transistor, or a diode.

[Production Process of Gas Detection Device and Operation Thereof]

An example of a process of producing the gas detection device 100 will now be described with reference to FIGS. 2A to 2G.

Figure 2A:
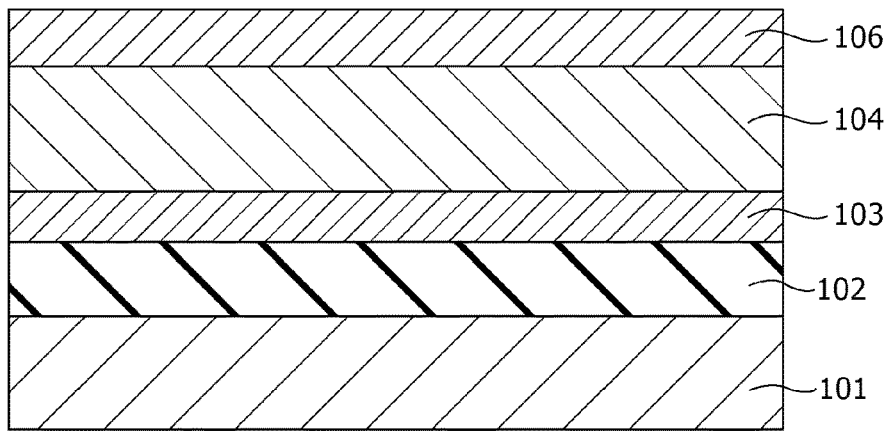
FIG. 2A is a cross-sectional view illustrating an example of a process of producing the gas detection device according to First Embodiment.

First, as shown in FIG. 2A, an insulation film 102 having a thickness of 200 nm is formed on a substrate 101 of, for example, single crystal silicon by a thermal oxidation method. Subsequently, a first electrode 103 of, for example, a Pt thin film having a thickness of 100 nm is formed on the insulation film 102 by sputtering. In addition, an adhesion layer of, for example, Ti or TiN may be formed between the first electrode 103 and the insulation film 102 by sputtering. An oxygen-deficient metal oxide layer, which becomes a resistive film 104, is then formed on the first electrode 103 by reactive sputtering using, for example, a Ta target. A resistive film 104 is thus formed.

Herein, an excessively large thickness of the resistive film 104 causes disadvantages, such as a too high initial resistance value, and an excessively small thickness causes a disadvantage of not giving a stable change in resistance. Accordingly, the thickness may be about 1 nm or more and about 8 nm or less.

Subsequently, a second electrode 106 of, for example, a Pt thin film having a thickness of 150 nm is formed on the resistive film 104 by sputtering.

Figure 2B:
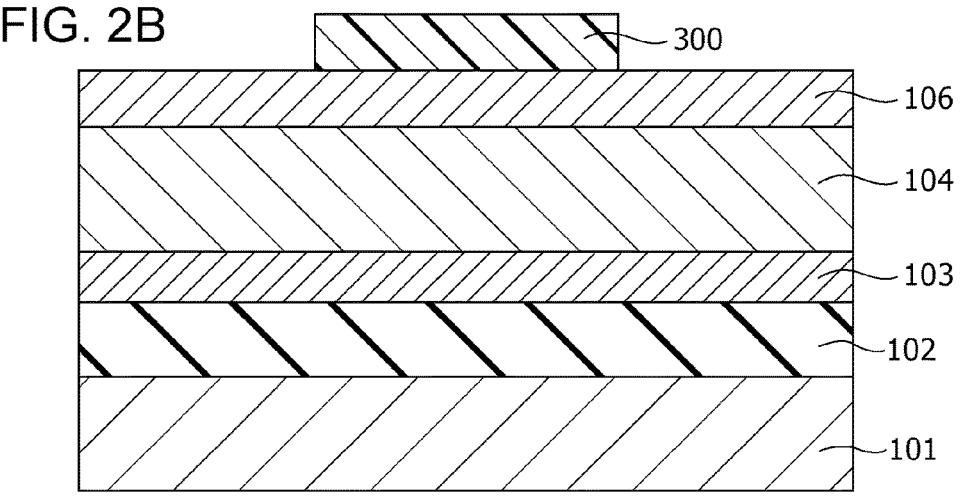
FIG. 2B is a cross-sectional view illustrating an example of the process of producing the gas detection device according to First Embodiment.
Figure 2C:
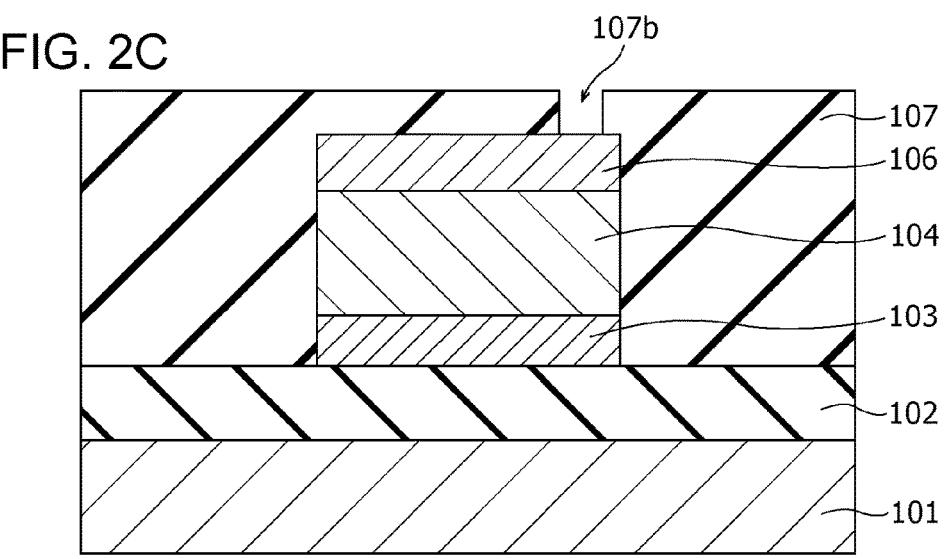
FIG. 2C is a cross-sectional view illustrating an example of the process of producing the gas detection device according to First Embodiment.

Subsequently, as shown in FIG. 2B, a photoresist mask 300 is formed by a photolithography process. Then, as shown in FIG. 2C, the first electrode 103, the resistive film 104, and the second electrode 106 are formed into the shape of the device by dry etching using the mask 300.

Figure 2D:
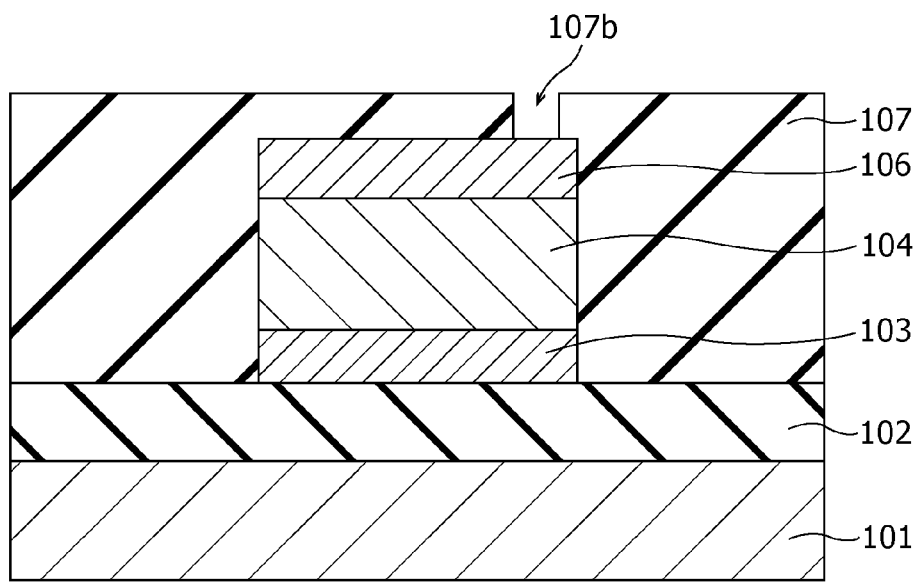
FIG. 2D is a cross-sectional view illustrating an example of the process of producing the gas detection device according to First Embodiment.

Then, as shown in FIG. 2D, an insulation film 107 is formed so as to cover the insulation film 102, the first electrode 103, the resistive film 104, and the second electrode 106. The insulation film 107 is then etched to form a via hole 107b reaching a part of the upper surface of the second electrode 106.

Figure 2E:
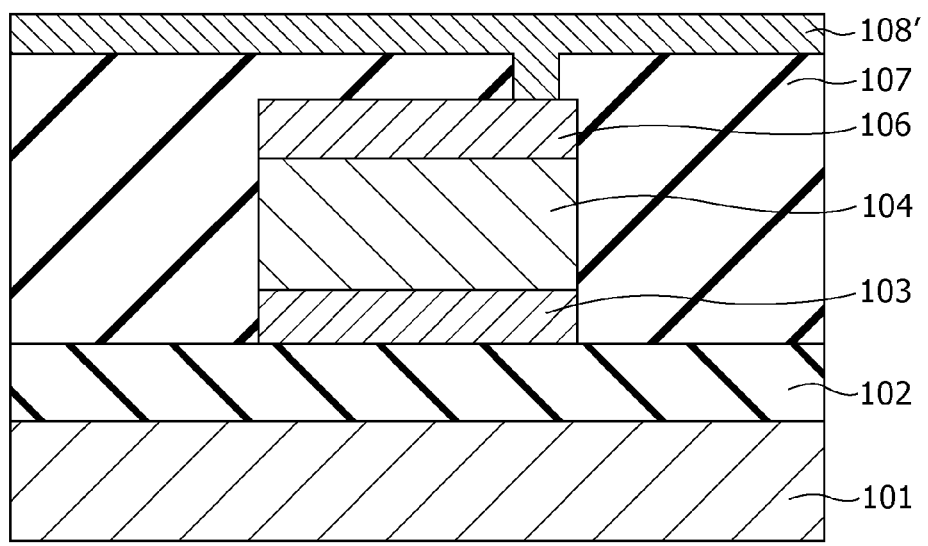
FIG. 2E is a cross-sectional view illustrating an example of the process of producing the gas detection device according to First Embodiment.
Figure 2F:
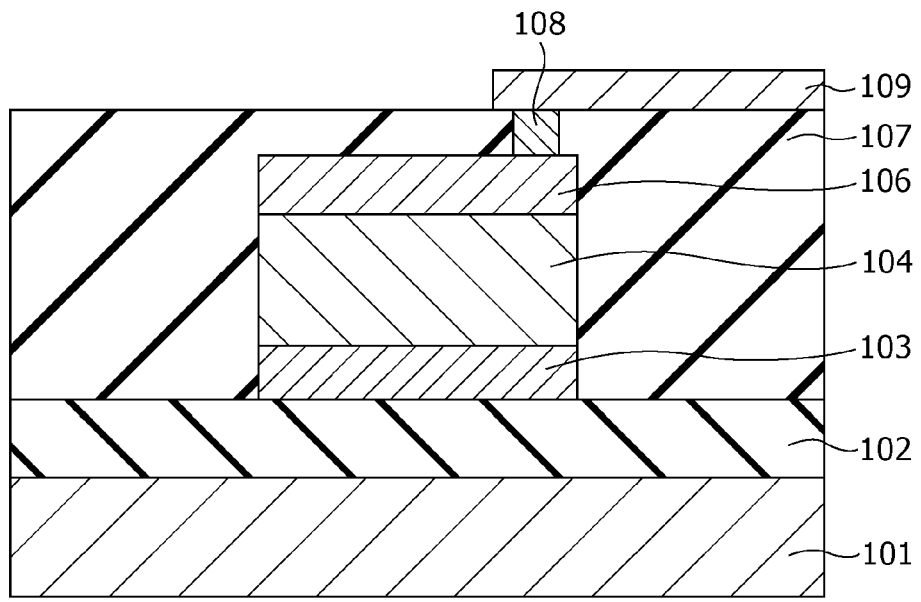
FIG. 2F is a cross-sectional view illustrating an example of the process of producing the gas detection device according to First Embodiment.

Subsequently, as shown in FIG. 2E, a conductor film 108' is formed on the upper surface of the insulation film 107 and the inside of the via hole 107b so as to fill the via hole 107b. Then, as shown in FIG. 2F, the conductor film 108' on the insulation film 107 is removed by chemical mechanical polishing (CMP) to form a via 108 in the via hole 107b. Another conductor film is further formed on the insulation film 107 and is patterned to form a wiring 109 connected to the via 108.

Figure 2G:
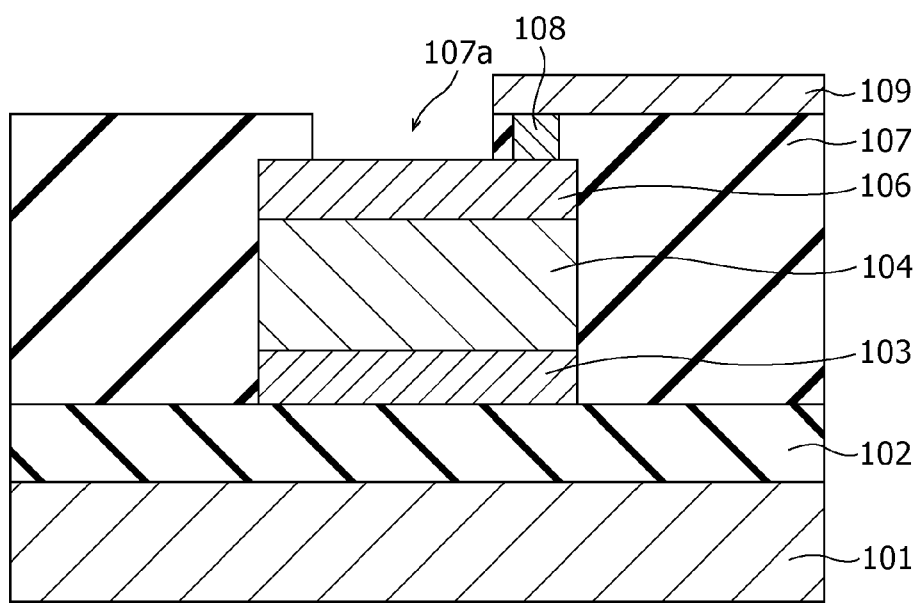
FIG. 2G is a cross-sectional view illustrating an example of the process of producing the gas detection device according to First Embodiment.

Subsequently, as shown in FIG. 2G, the insulation film 107 is etched to form an opening 107a exposing a part of the upper surface of the second electrode 106.

Subsequently, an initial break voltage is applied between the first electrode 103 and the second electrode 106 to form a local area 105 shown in FIG. 1A in the resistive film 104. A gas detection device 100 is thus produced.

The characteristics of the gas detection device 100 of changing the resistance by voltage application will now be described based on the results of actual measurement using a sample device. The characteristics of the gas detection device 100 of changing the resistance by hydrogen-containing gas will be described below.

Figure 3:
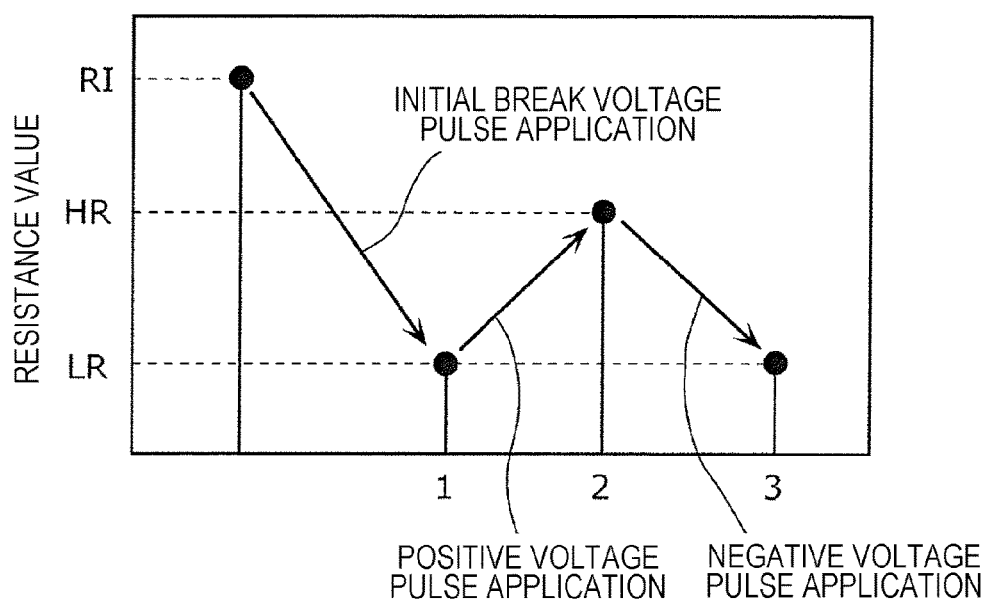
FIG. 3 is a diagram illustrating an example of the state transition of the gas detection device according to First Embodiment.

FIG. 3 is a graph showing the resistance change characteristics actually measured using a sample device.

In the gas detection device 100 as the sample device giving the measurement results shown in FIG. 3, the first electrode 103, the second electrode 106, and the resistive film 104 each have a size of 0.5 μm×0.5 μm (area: 0.25 μm$^2$); the value of y of TaOy representing the composition of tantalum oxide constituting the resistive film 104 is 2.47; and the resistive film 104 has a thickness of 5 nm. In such a gas detection device 100, if a read-out voltage (e.g., 0.4 V) is applied between the first electrode 103 and the second electrode 106, the initial resistance value RI is about $10^7$ to $10^8 \Omega$.

As shown in FIG. 3, if the resistance value of the gas detection device 100 is an initial resistance value RI (a value higher than the resistance value HR in the high resistive state), the resistive state changes by application of an initial break voltage between the first electrode 103 and the second electrode 106. Subsequently, as shown in FIG. 3, the resistance value between the first electrode 103 and the second electrode 106 changes by alternate application of, for example, two kinds of voltage pulses each having a pulse width of 100 ns and having different polarities (a positive voltage pulse and a negative voltage pulse), as a write-in voltage, between the first electrode 103 and the second electrode 106 of the gas detection device 100.

That is, application of a positive voltage pulse (pulse width: 100 ns) as the write-in voltage between the electrodes increases the resistance value between the first electrode 103 and the second electrode 106 from the low resistance value LR to the high resistance value HR. In contrast, application of a negative voltage pulse (pulse width: 100 ns) as the write-in voltage between the electrodes decreases the resistance value between the first electrode 103 and the second electrode 106 from the high resistance value HR to the low resistance value LR. The polarity of a voltage pulse is "positive" if the potential of the second electrode 106 is higher than that of the first electrode 103 as a reference and is "negative" if the potential of the second electrode 106 is less than that of the first electrode 103 as a reference.

By utilizing such characteristics of changing resistance by voltage application, hydrogen-containing gas can be detected with the gas detection device 100 set to the high resistive state (HR) before the start of monitoring of hydrogen-containing gas by applying a positive voltage pulse between the first electrode 103 and the second electrode 106. In such a case, a reduction in the resistance value can be more clearly detected, compared to the case of detecting hydrogen-containing gas with the gas detection device 100 in the low resistive state (LR), and thereby the characteristics of detecting hydrogen-containing gas are improved.

[Modification of Gas Detection Device]

Figure 4:
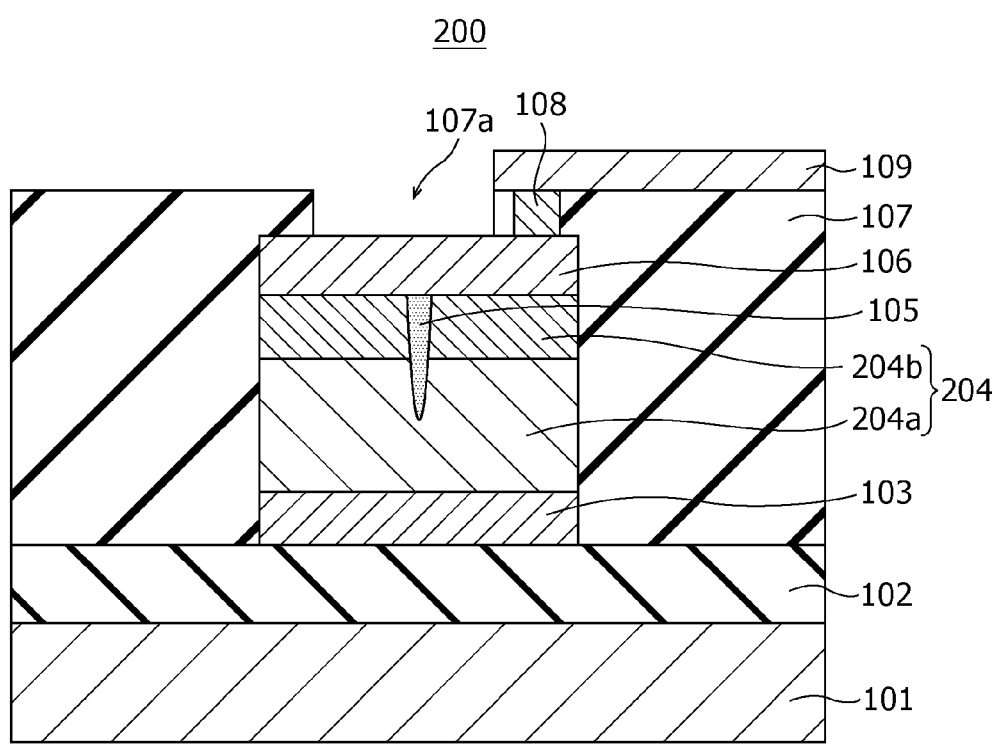
FIG. 4 is a cross-sectional view illustrating a gas detection device according to a modification of First Embodiment.

FIG. 4 is a cross-sectional view illustrating an example of the structure of a gas detection device according to a modification of First Embodiment. Only the points different from the gas detection device 100 of First Embodiment will now be described.

The gas detection device 200 of the modification differs from the gas detection device 100 of First Embodiment in that the resistive film 204 is a laminate of a first metal oxide layer 204a being in contact with the first electrode 103 and a second metal oxide layer 204b being in contact with the second electrode 106. The resistive film 204 is not limited to a laminate of two layers and may be a laminate of three or more layers.

The first metal oxide layer 204a and the second metal oxide layer 204b include a local area 105 that reversibly changes the degree of oxygen deficiency depending on application of an electric pulse and hydrogen-containing gas. The local area 105 at least passes through the second metal oxide layer 204b and is in contact with the second electrode 106.

In other words, the resistive film 204 includes a layered structure at least composed of a first metal oxide layer 204a containing a first metal oxide and a second metal oxide layer 204b containing a second metal oxide. The first metal oxide layer 204a is disposed between the first electrode 103 and the second metal oxide layer 204b, and the second metal oxide layer 204b is disposed between the first metal oxide layer 204a and the second electrode 106.

The second metal oxide layer 204b may have a thickness smaller than that of the first metal oxide layer 204a. In such a case, a structure including the local area 105 not being in contact with the first electrode 103 can be readily formed. The second metal oxide layer 204b may have a degree of oxygen deficiency less than that of the first metal oxide layer 204a. In such a case, the resistance value of the second metal oxide layer 204b is higher than that of the first metal oxide layer 204a. Accordingly, most of the voltage applied to the resistive film 204 is applied to the second metal oxide layer 204b. This structure is useful for, for example, concentrating the initial break voltage in the second metal oxide layer 204b and reducing the initial break voltage necessary for forming the local area 105.

In the present disclosure, if the metals constituting the first metal oxide layer 204a and the second metal oxide layer 204b are the same, the term "oxygen content" may be used instead of the term "degree of oxygen deficiency". A "high oxygen content" corresponds to a "low degree of oxygen deficiency", and a "low oxygen content" corresponds to a "high degree of oxygen deficiency".

However, as described below, the resistive film 204 according to this embodiment is not limited to the case that the metals constituting the first metal oxide layer 204a and the second metal oxide layer 204b are the same, and the metals may be different from each other. That is, the first metal oxide layer 204a and the second metal oxide layer 204b may be made of different metal oxides.

If the first metal constituting the first metal oxide layer 204a and the second metal constituting the second metal oxide layer 204b are the same, the oxygen content has a corresponding relationship with the degree of oxygen deficiency. That is, if the oxygen content of the second metal oxide is higher than that of the first metal oxide, the second metal oxide has a degree of oxygen deficiency less than that of the first metal oxide.

The resistive film 204 includes a local area 105 in the vicinity of the interface between the first metal oxide layer 204a and the second metal oxide layer 204b. The local area 105 has a degree of oxygen deficiency higher than that of the second metal oxide layer 204b and is different from that of the first metal oxide layer 204a.

The local area 105 is formed in the resistive film 204 by applying an initial break voltage between the first electrode 103 and the second electrode 106. The initial break voltage forms the local area 105 being in contact with the second electrode 106, passing through the second metal oxide layer 204b, partially penetrating into the first metal oxide layer 204a, and being not in contact with the first electrode 103.

An example of evaluating the characteristics of the thus-structured gas detection device 200 of changing the resistance by hydrogen-containing gas will now be described.

Figure 5:
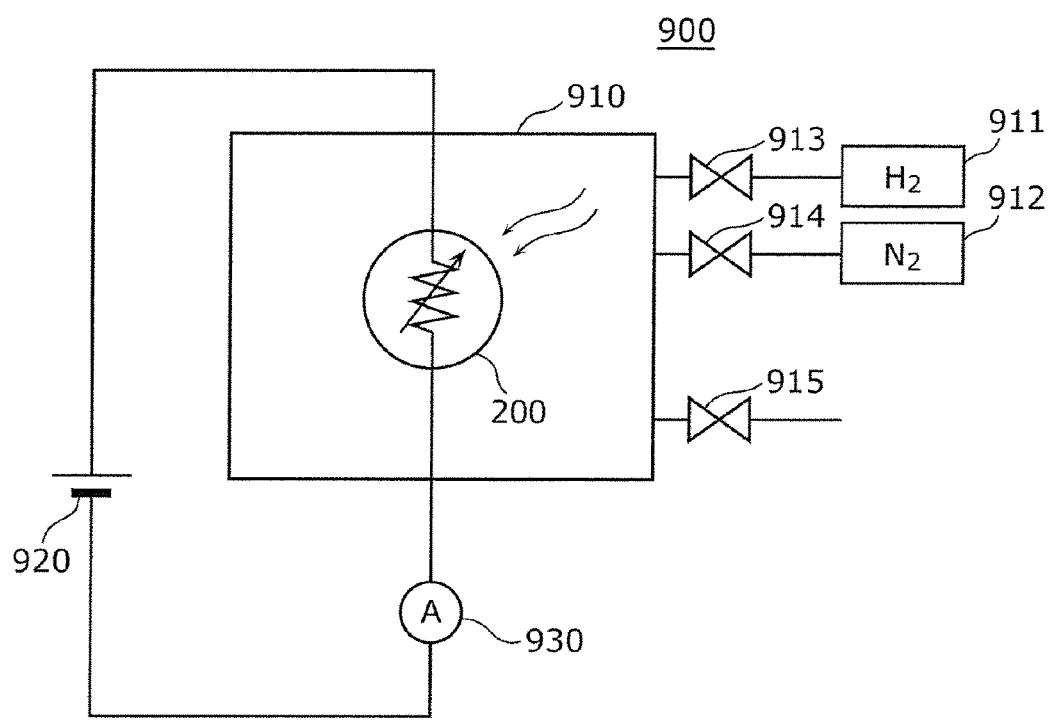
FIG. 5 is a diagram illustrating an evaluation system of the gas detection device according to the modification of First Embodiment.

FIG. 5 is a block diagram illustrating an example of an evaluation system used for evaluating the gas detection device 200. The evaluation system 900 shown in FIG. 5 includes an airtight container 910 accommodating the gas detection device 200, a detection power supply 920 generating a detection voltage, and a current meter 930. The airtight container 910 is connected to a hydrogen cylinder 911 and a nitrogen cylinder 912 through introduction valves 913 and 914, respectively, and is configured such that the gas in the inside can be exhausted through an exhaust valve 915.

Figure 6:
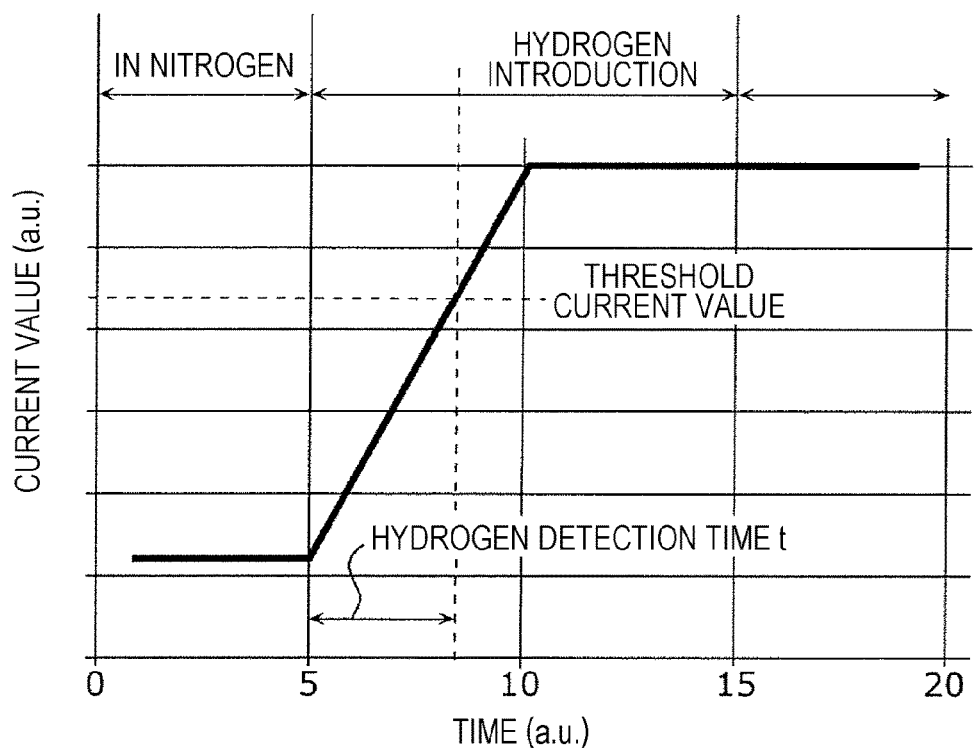
FIG. 6 is a diagram illustrating the results of evaluation of the gas detection device according to a modification of the basic structure.

FIG. 6 is a graph showing an example of evaluating the gas detection device 200. The horizontal axis indicates the time (arbitrary unit: a.u.), and the vertical axis indicates the value (a.u.) of current flowing in the gas detection device 200. In the experiment, the gas detection device 200 was placed in the nitrogen gas introduced into the airtight container 910, and the measurement of current was started by application of a detection voltage. Subsequently, hydrogen gas was introduced into the airtight container 910.

FIG. 6 shows the results of the above experiment. The horizontal axis indicates the two periods of in nitrogen and introduction of hydrogen. The current value starts to increase after the start of introduction of hydrogen gas, and the hydrogen gas is detected by that the current value reaches a predetermined threshold current value. The time for increasing the current value from that at the start of introduction of hydrogen gas to the predetermined threshold current value is represented by hydrogen detection time t. After the detection of hydrogen, the current value further increases to saturation.

It is known that the hydrogen detection time t becomes longer with a decrease in the concentration of hydrogen contained in the gas as an object to be tested and becomes shorter with an increase in the concentration of hydrogen. That is, the hydrogen detection time t is an index of time sensitivity directly showing the time necessary for detecting hydrogen gas having a certain hydrogen concentration and also an index of concentration sensitivity associated with the lower limit of the hydrogen concentration of hydrogen-containing gas detectable within a practical limited time.

In this example of evaluation, the gas detection device 200 was used after application of a predetermined voltage (reset voltage) between the first electrode 103 and the second electrode 106 to previously set the local area 105 to a high resistive state.

In the monitoring behavior for hydrogen-containing gas, a detection voltage of 0.6 V was applied between the first electrode 103 and the second electrode 106 to detect hydrogen gas, and in the state that the current value was saturated, a current of about 20 μA flowed between the first electrode 103 and the second electrode 106.

It is therefore demonstrated that the gas detection device 200 can monitor hydrogen-containing gas with a very small power consumption of 0.012 mW at the highest. This voltage of 0.6 V may be applied at all times between the first electrode 103 and the second electrode 106.

In the case of applying a detection voltage of 0.4 V between the first electrode 103 and the second electrode 106, a change in resistance by hydrogen gas was not caused, and the hydrogen gas could not be detected. This was probably caused by that the heat generation in the local area 105 by application of a detection voltage of 0.4 V was insufficient for accelerating the catalytic action of the second electrode 106 and application of a detection voltage of 0.6 V is necessary for enabling the detection of hydrogen gas. The detection voltage of 0.6 V in this case is an example of the detection voltage for activating the characteristics of decreasing the resistance value between the first electrode 103 and the second electrode 106 by the contact of the second electrode 106 with gas including gas molecules containing hydrogen atoms.

In the gas detection device 200, after the detection of hydrogen-containing gas and an increase in the current value to saturation, i.e., after detection of hydrogen-containing gas and change to a low resistive state of the gas detection device 200, the local area 105 can be reset to the high resistive state by applying a predetermined voltage (reset voltage) between the first electrode 103 and the second electrode 106.

Figure 7:
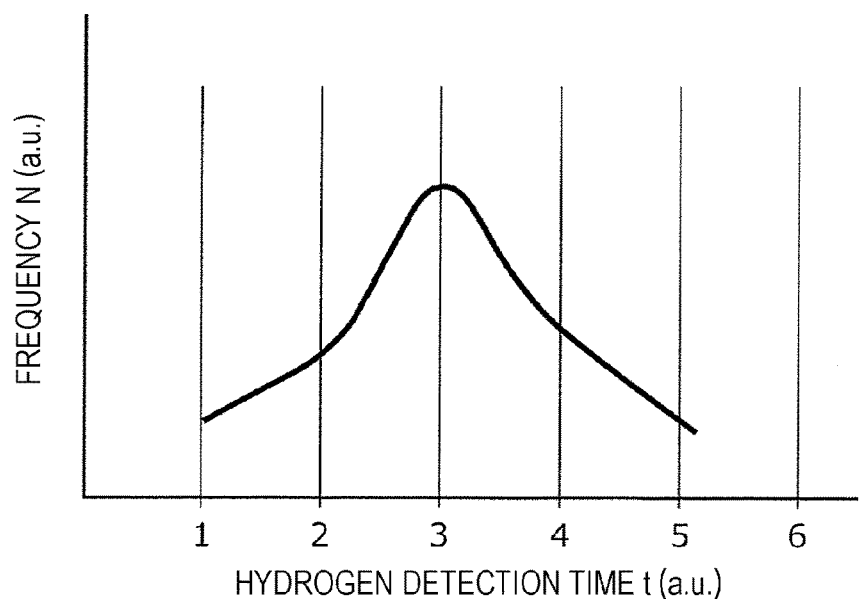
FIG. 7 is a graph showing the distribution of hydrogen detection time in the results of evaluation performed multiple times for the gas detection device according to the modification of the basic structure.

FIG. 7 shows the frequency distribution of hydrogen detection time t (a.u.) in a case of repeating for a predetermined times (for example, 50 times) an experiment of detecting hydrogen-containing gas with the gas detection device 200 again after the reset of the local area 105 to the high resistive state.

FIG. 7 demonstrates that the hydrogen detection time t varies in each hydrogen detection behavior according to a certain distribution when the gas detection device 200 repeats the hydrogen detection behavior. In also the case of simultaneously performing the hydrogen detection behavior with a plurality of the gas detection devices 200, the hydrogen detection time t varies in each hydrogen-detecting device according to a similar distribution.

From the results described above, the inventors presume the mechanism of the variation in the hydrogen detection time t in the gas detection device 200 as follows.

The contact of the second electrode 106 with hydrogen-containing gas releases hydrogen atoms from the hydrogen-containing gas by the catalytic action of the second electrode 106. The released hydrogen atoms diffuse in the second electrode 106 for maintaining the equilibrium state and reach the local area 105.

It is inferred that the hydrogen atoms reached the local area 105 cause a redox reaction in the minute local area 105 and react with oxygen in the local area 105 to newly generate oxygen defects in the local area 105 and increase the degree of oxygen deficiency in the local area 105; the generation of a large number of oxygen defects in the local area 105 allows the filaments formed from the oxygen defects to be readily connected to one another to reduce the resistance value of the local area 105; and as a result, the current flowing between the first electrode 103 and the second electrode 106 is increased.

It is, however, inferred that oxygen defects occur at random positions in the local area 105; even if the numbers of oxygen defects are the same, filaments are easily connected or not easily connected to one another depending on the positions where the oxygen defects are formed; an increase in current is rapidly caused when the oxygen defects are formed at positions allowing easy connection of filaments and is slowly caused when the oxygen defects are formed at positions not allowing easy connection of filaments; and as a result, hydrogen detection time t varies.

It is inferred that the above-described behavior is not limited to the gas detection device 200 and also occurs in the gas detection device 100 or another gas detection device described below having the same structure as that of the gas detection device 200. It is also inferred that the above-described behavior is not limited to detection of hydrogen gas and occurs in a variety of hydrogen-containing gases, such as methane and alcohol.

The variation in the hydrogen detection time t impedes the sensitivity and stability in detection of hydrogen-containing gas by the gas detection device. Specifically, it is concerned that the time necessary for detecting hydrogen-containing gas of a certain hydrogen concentration becomes unstable (deterioration in time sensitivity) or the lower limit of hydrogen concentration of hydrogen-containing gas that can be detected within an actual time limit becomes unstable (deterioration in concentration sensitivity).

That is, a single gas detection device 200 generates heat by only the current for detecting the resistive state and has excellent power-saving properties allowing detection of hydrogen-containing gas without heating with a separate heater, but has a disadvantage of lacking in the stability of detection sensitivity.

Accordingly, as a countermeasure for this disadvantage, proposed is a gas sensor including a plurality of gas detection devices having the same structure and the same size and detecting hydrogen-containing gas through a reduction in the resistance value between the first electrode and the second electrode in a predetermined number of the plurality of gas detection devices.

[Structure of Gas Sensor]

Figure 8:
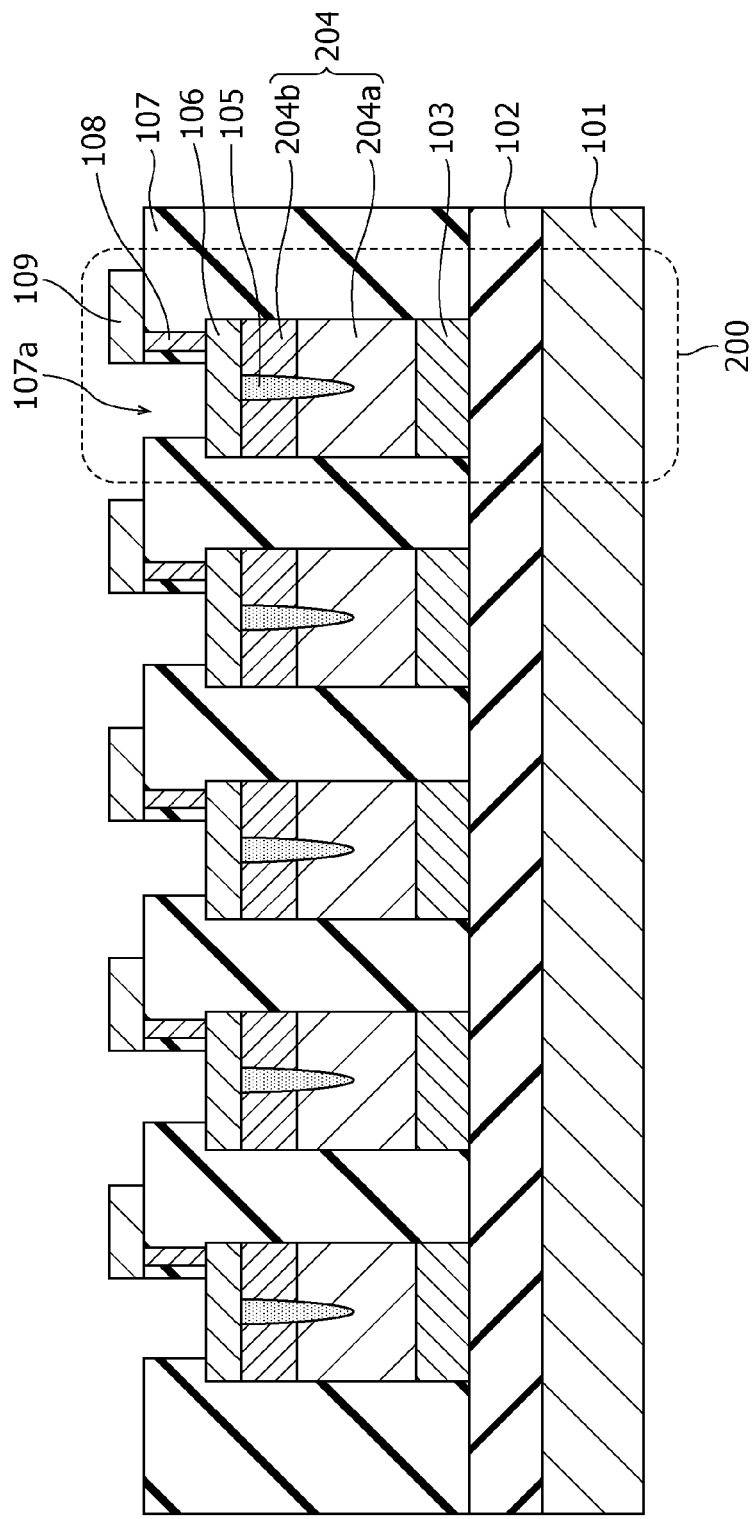
FIG. 8 is a cross-sectional view illustrating an example of a gas sensor according to First Embodiment.

FIG. 8 is a cross-sectional view illustrating an example of the structure of a gas sensor 1000 according to First Embodiment. The gas sensor 1000 includes a plurality of the gas detection devices 200 disposed on a substrate 101. FIG. 8 shows an example of disposing five gas detection devices 200. The gas detection devices 200 constituting the gas sensor 1000 have the same structure and the same size.

Herein, the term "the same structure" refers to that, for example, the order of lamination of components and the materials used are the same, and the term "the same size" refers to that, for example, the design dimensions are the same. In an actually produced gas sensor 1000, the materials and the shape sizes may have slight errors (e.g., an error of about several percent).

[Production Process of Gas Sensor]

The gas sensor 1000 is produced by basically the same process as that of producing the gas detection device 100 shown in FIGS. 2A to 2G. The details of the step shown in FIG. 2A are changed such that a resistive film 204 is formed by laminating two layers, a first metal oxide layer 204a and a second metal oxide layer 204b. The gas sensor 1000 including a plurality of gas detection devices 200 shown in FIG. 8 is produced by batch formation of the gas detection devices 200.

[Gas Detection Circuit]

Figure 9:
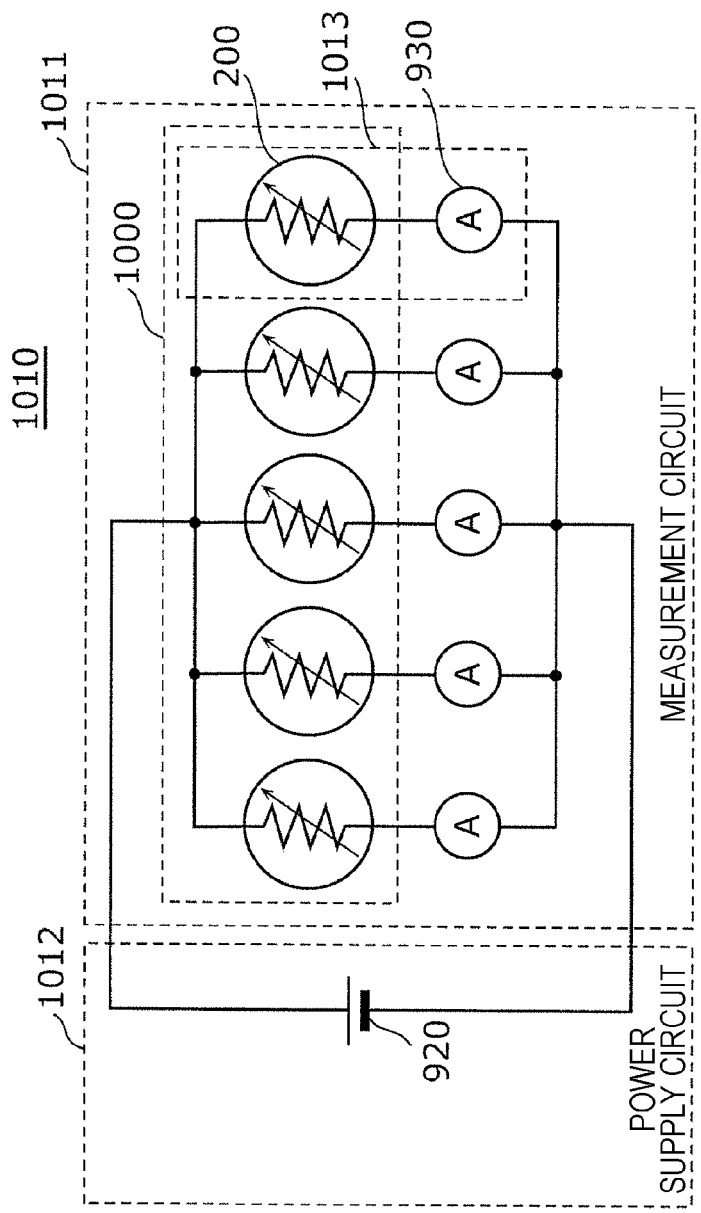
FIG. 9 is a circuit diagram illustrating an example of a gas detection circuit according to First Embodiment.

FIG. 9 is a circuit diagram illustrating an example of a gas detection circuit 1010 including the gas sensor 1000 according to First Embodiment.

The gas detection circuit 1010 includes a measurement circuit 1011 including a plurality of series circuits 1013 that are each composed of a current meter 930 and a gas detection device 200 connected to each other in series and are connected in parallel to one another and a power supply circuit 1012 including a detection power supply 920. The current meters 930 measure the current flowing in the respective gas detection devices connected to the corresponding current meters 930 when a detection voltage is applied between the first electrode and the second electrode of each of the gas detection devices 200 by the detection power supply 920.

In the gas detection circuit 1010, hydrogen-containing gas is detected through increases in current in a predetermined number of the current meters 930 (i.e., decreases in the resistance values of the predetermined number of the gas detection devices 200). The predetermined number may be one or two or more.

More specifically, the second electrodes 106 of the gas detection devices 200 are connected to one another through the via 108 and the wiring 109 shown in FIG. 8 and are connected to the plus potential terminal of the detection power supply 920. The first electrodes 103 of the gas detection devices 200 are respectively connected to one ends of the corresponding current meters 930 through, for example, wirings (not shown). The other ends of the current meters 930 are connected to the minus potential terminal of the detection power supply 920. In this structure, the detection power supply 920 applies a detection voltage between the first electrode 103 and the second electrode 106 of each of the gas detection devices 200.

In the gas detection circuit 1010, the decision point of hydrogen detection is the time at which the current in one of the current meters 930 connected to the respective gas detection devices 200 exceeds a predetermined threshold current value shown in FIG. 6 at first after the start of introduction of hydrogen gas. That is, the gas detection circuit 1010 decides the detection of hydrogen at the time at which the current in the first one among the gas detection devices 200 exceeds a predetermined threshold current value.

Figure 10A:
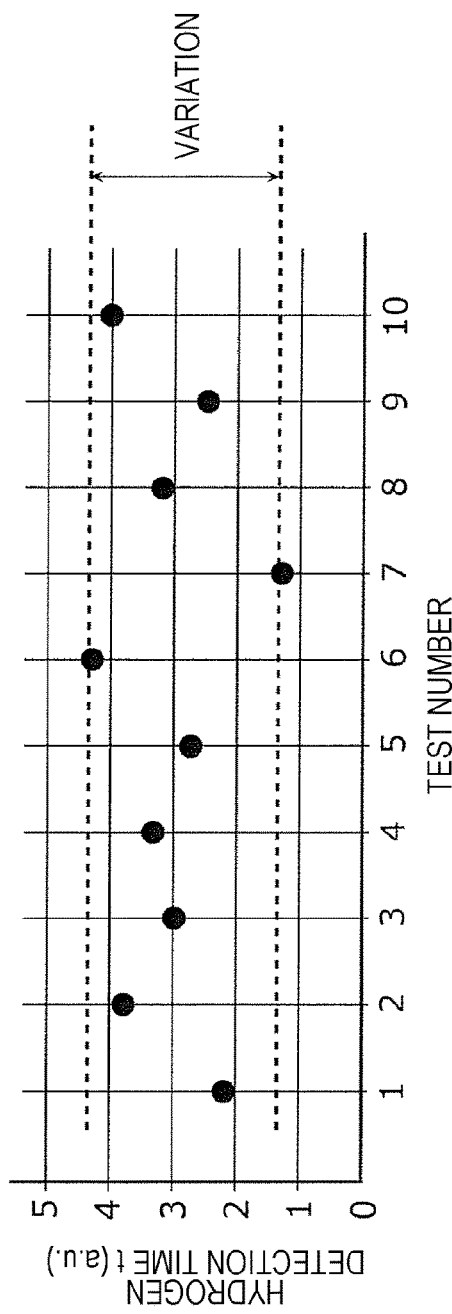
FIG. 10A is a graph showing the variation in each test of hydrogen detection time of a gas detection device according to First Embodiment.

FIG. 10A a graph showing the variation in each test of hydrogen detection time t of the gas detection device 200 and shows the results of measurement of the hydrogen detection time t with a single gas detection device 200 for multiple times under the same experimental conditions using the evaluation system 900 shown in FIG. 5. In FIG. 10A, the horizontal axis indicates the test number of the gas detection device 200 used in each experiment. The vertical axis indicates the hydrogen detection time t (a.u.). FIG. 10A shows that the hydrogen detection time t highly varies in each test and demonstrates that the sensitivity of detecting hydrogen is very unstable.

Figure 10B:
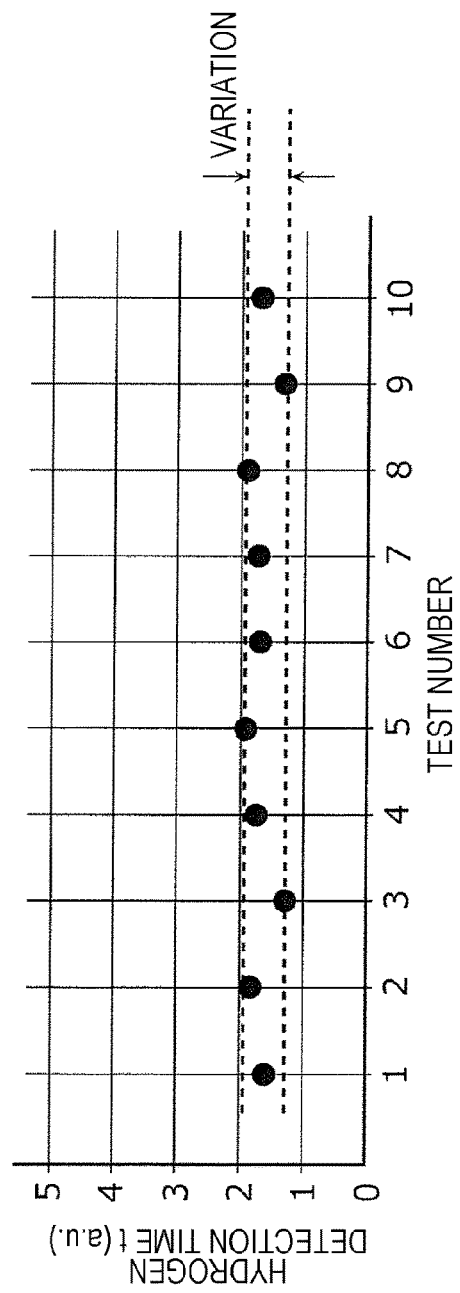
FIG. 10B is a graph showing the variation in each test of hydrogen detection time of a gas sensor according to First Embodiment.

FIG. 10B is a graph showing the variation in each test of hydrogen detection time t of a gas sensor 1000 and shows the results of measurement of the hydrogen detection time t performed for multiple times under the same experimental conditions using the gas detection circuit 1010 including the gas sensor 1000 shown in FIG. 9. The hydrogen detection time t in FIG. 10B is the shortest hydrogen detection time t in those of the plurality of gas detection devices 200 constituting the gas sensor 1000. The level and the variation in the hydrogen detection time t in the gas sensor 1000 are both lower than those in a single gas detection device 200. That is, high sensitivity of detecting hydrogen can be stably achieved.

As described above, the gas detection circuit 1010 using the gas sensor 1000 including a plurality of the gas detection devices 200 having the same structure and the same size can perform stable detection of hydrogen. Although the experimental results in hydrogen gas have been described in the embodiment, the same advantageous effects as those in hydrogen gas are also observed in gas containing hydrogen (e.g., ammonium gas).

[Supplement]

Figure 14:
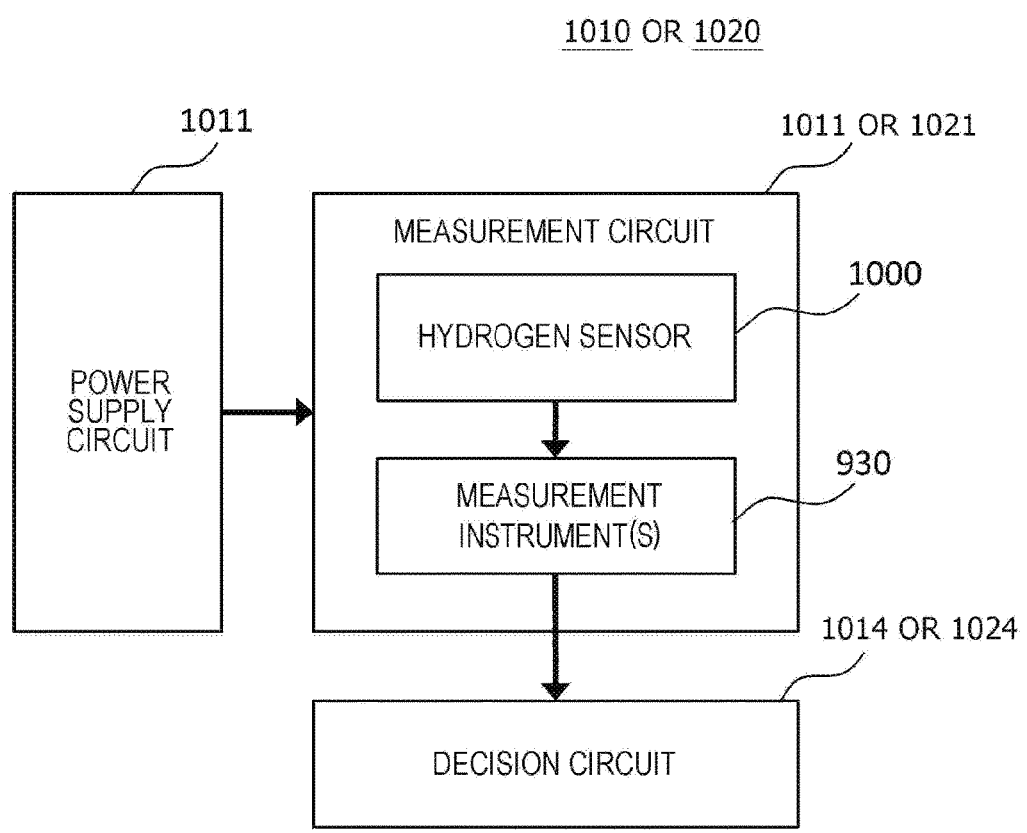
FIG. 14 is a schematic diagram illustrating an example of a gas detection circuit according to First, Second, or Third Embodiment.

As shown in FIGS. 9 and 14, the gas detection circuit 1010 includes a measurement circuit 1011 including the gas sensor 1000 and a plurality of current meters 930 and includes a decision circuit 1014. The gas detection circuit 1010 is an example of the "gas-detecting apparatus" in the present disclosure, and the current meter 930 is an example of the "measurement instrument" in the present disclosure.

As shown in FIG. 8, the gas sensor 1000 includes a plurality of gas detection devices 200 covered with an insulation film 107. The gas detection device 200 is an example of the "detection cell" in the present disclosure.

Each of the gas detection devices 200 includes a first electrode 103, a resistive film disposed on the first electrode 103, and a second electrode 106 disposed on the resistive film 204. The resistive film 204 is an example of the "metal oxide layer" of the present disclosure. The resistive film 204 includes a first metal oxide layer 204a and a second metal oxide layer 204b. The resistive film 204 includes a local area 105 and a bulk area surrounding the local area 105. Herein, the term "surrounding the local area 105" is not limited to entirely surrounding the outer periphery of the local area 105. In FIG. 8, the bulk area is the region of the second metal oxide layer 204b excluding the local area 105. The local area 105 has a degree of oxygen deficiency higher than that of the bulk area. The first metal oxide layer 204a has a degree of oxygen deficiency higher than that of the bulk area. In FIG. 8, the local area 105 is in contact with the second electrode 106, passes through the second metal oxide layer 204b, and is not in contact with the first electrode 103.

In FIG. 8, the insulation film 107 includes an opening 107a. In the opening 107a, a part of the upper surface of the second electrode 106 is exposed from the insulation film 107. The exposed surface of the second electrode 106 is allowed to come into contact with gas.

The contact of the second electrode 106 with gas containing hydrogen atoms decreases the resistance value of the local area 105, decreases the resistance value of the resistive film 204, and decreases the resistance value of the gas detection device 200.

In FIG. 9, the current meters 930 are respectively connected in series to the corresponding gas detection devices 200 in one-to-one relationship. As a result, the current meters 930 concurrently monitor each of the current values flowing in the gas detection devices 200 to concurrently monitor a plurality of the resistance values of the gas detection device 200. In the present disclosure, the term "monitoring the resistance value" means that physical quantity (e.g., current value or voltage value) relating to a resistance value is continuously or intermittently measured to continuously or intermittently obtain the information on the resistance value. In the present disclosure, the term "concurrently monitoring a plurality of resistance values" means that the periods of time for monitoring each resistance value are partially or entirely overlapped with one another. For example, the term "concurrently monitoring a plurality of resistance values" includes a procedure of repeating a sequence of sequentially obtaining information on the resistance values from a plurality of the gas detection devices 200 for a predetermined period of time.

The current meter 930 includes, for example, a capacitor connected in series or in parallel to the gas detection device 200, a switch connected between the gas detection device 200 and the capacitor, and a timer. For example, during the On-state of the switch, current flows from the gas detection device 200 to the capacitor to accumulate the charge in the capacitor. The accumulated charge is then allowed to flow out from the capacitor to reduce the voltage applied to the capacitor. The timer measures the time from the release of the charge of the capacitor until a reduction of the voltage of the capacitor to a predetermined level or less. Herein, the rate of voltage decrease reflects the resistance value of the gas detection device 200 through the amount of charge accumulated in the capacitor and the amount of current flew from the gas detection device 200. Accordingly, the time measured by the timer includes the information on the resistance value. The timer may be, for example, a counter. Alternatively, the current meter 930 may be an ammeter.

Alternatively, voltmeters may be connected in parallel to both ends of the individual detection devices to obtain the information on the resistance value through the voltage measurement.

The decision circuit 1014 decides whether the measurement circuit 1011 has detected gas containing hydrogen atoms or not based on at least one change of the resistance values of the plurality of gas detection devices 200. For example, if the measurement circuit 1011 includes N gas detection devices 200 (N is an integer of two or more), the decision circuit 1014 decides the detection of hydrogen-containing gas when M of the resistance values (M is an integer of one or more and less than N) of the N gas detection devices 200 (N is an integer of two or more) are decreased. For example, M may be an integer of two or more. The decision circuit 1014 may, for example, obtain a measured value from the current meter 930 and compare the measured value with a predetermined threshold value. The decision circuit 1014 includes, for example, a semiconductor device, a semiconductor integrated circuit (IC), a large scale integration (LSI), or an electronic circuit of a combination thereof. The LSI or IC may be integrated on one chip, or a plurality of chips may be combined. The LSI or IC can be called, for example, a system LSI, a very large scale integration (VLSI), or an ultra large scale integration (ULSI) depending on the degree of integration. The decision circuit 1014 may include a comparator for comparing a measured value and a fixed value (e.g., threshold value). The decision circuit 1014 is, for example, a microcomputer. At least a part of the decision circuit 1014 and the measurement circuit 1011 may be integrated on one chip.

Second Embodiment

Figure 11:
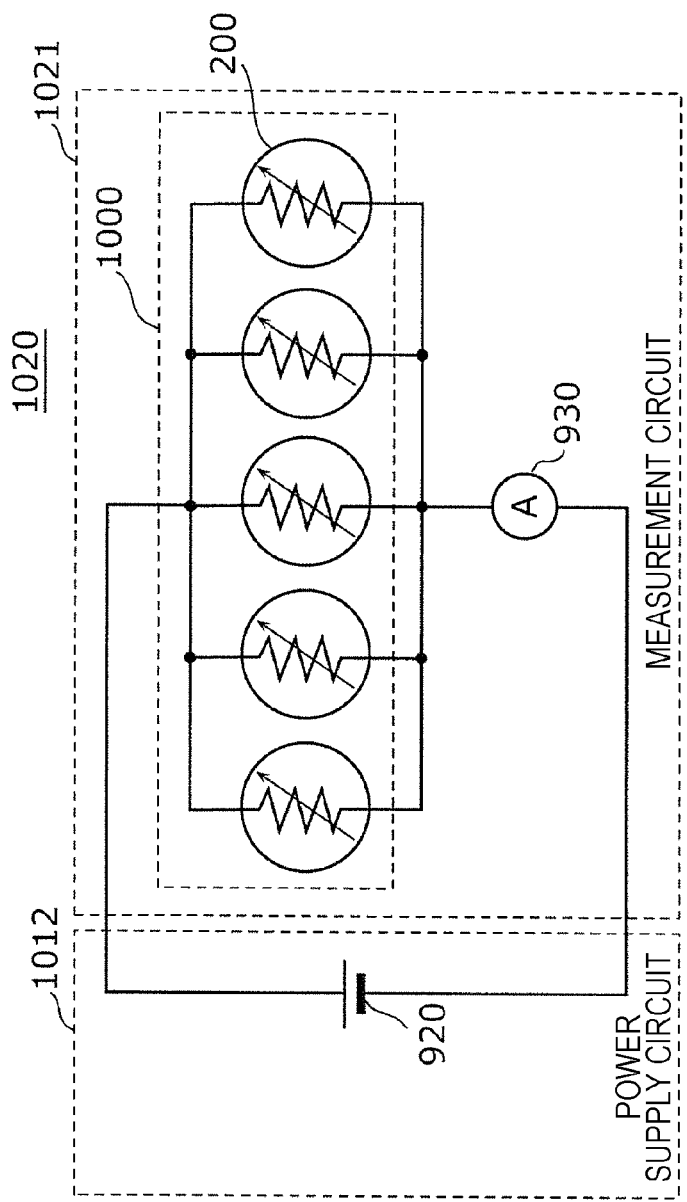
FIG. 11 is a circuit diagram illustrating an example of a gas detection circuit according to Second Embodiment.

FIG. 11 is a circuit diagram illustrating an example of a gas detection circuit 1020 including a gas sensor 1000 according to Second Embodiment.

The gas detection circuit 1020 includes a measurement circuit 1021 composed of a parallel circuit (i.e., gas sensor 1000) composed of a plurality of gas detection devices 200 connected in parallel and a current meter 930 connected in series to the parallel circuit; and a power supply circuit 1012 including a detection power supply 920. The current meter 930 measures the current flowing in the gas sensor 1000 when the detection power supply 920 applies a detection voltage between the first electrode and the second electrode of each of the gas detection devices 200.

In the gas detection circuit 1020, hydrogen-containing gas is detected through an increase in the current measured by the current meter 930 in an amount corresponding to the reduction of the resistance values in a predetermined number of the plurality of gas detection devices 200. The predetermined number may be one or two or more.

More specifically, the second electrodes 106 of the gas detection devices 200 are connected to one another through the via 108 and the wiring 109 shown in FIG. 8 and are connected to the plus potential terminal of the detection power supply 920. The first electrodes 103 of the gas detection devices 200 are connected to one end of the current meter 930 through, for example, a wiring (not shown). The other end of the current meter 930 is connected to the minus potential terminal of the detection power supply 920. In this structure, the detection power supply 920 applies a detection voltage between the first electrode 103 and the second electrode 106 of each of the gas detection devices 200.

In the gas detection circuit 1020, the decision point of hydrogen detection is the time at which the current value of the current meter 930 exceeds a predetermined threshold current value shown in FIG. 6 after the start of introduction of hydrogen gas. The current flowing in the gas sensor 1000 increases at the timing at which the current flowing in the first one among the gas detection devices 200 exceeds a predetermined threshold current value shown in FIG. 6. As a result, the current value detected by the current meter 930 increases at this timing. Accordingly, the gas detection circuit 1020 decides the detection of hydrogen at the time at which the current in the first one among the gas detection devices 200 exceeds a predetermined threshold current value.

As described above, as in the gas detection circuit 1010, the gas detection circuit 1020 using the gas sensor 1000 including a plurality of the gas detection devices 200 having the same structure and the same size can perform stable detection of hydrogen. Although the experimental results in hydrogen gas have been described in the embodiment, the same advantageous effects as those in hydrogen gas are also observed in gas containing hydrogen (e.g., ammonium gas).

[Supplement]

As shown in FIGS. 11 and 14, the gas detection circuit 1020 includes a measurement circuit 1021 including a gas sensor 1000 and one current meter 930; and a decision circuit 1024. The gas detection circuit 1020 is an example of the "gas-detecting apparatus" in the present disclosure, and the current meter 930 is an example of the "measurement instrument" in the present disclosure.

In FIG. 11, the gas sensor 1000 is a parallel circuit composed of a plurality of gas detection devices 200 connected in parallel. The current meter 930 is connected in series to this parallel circuit. As a result, the current meter 930 can monitor the combined resistance value of the gas detection devices 200 by monitoring the combined current value flowing in the parallel circuit. In the present disclosure, the term "monitoring resistance values" is not limited to individual monitoring of resistance values and can include collective monitoring of resistance values.

The decision circuit 1024 detects at least a partial change of the resistance values of the plurality of gas detection devices 200 through a change in the combined resistance value of the plurality of gas detection devices 200. The decision circuit 1024 then decides, based on this change, whether the measurement circuit 1021 has detected gas containing hydrogen atoms or not. The decision circuit 1024 may obtain, for example, a measured value from the current meter 930 and may compare the resulting measured value with a plurality of threshold values.

Third Embodiment

Figure 12:
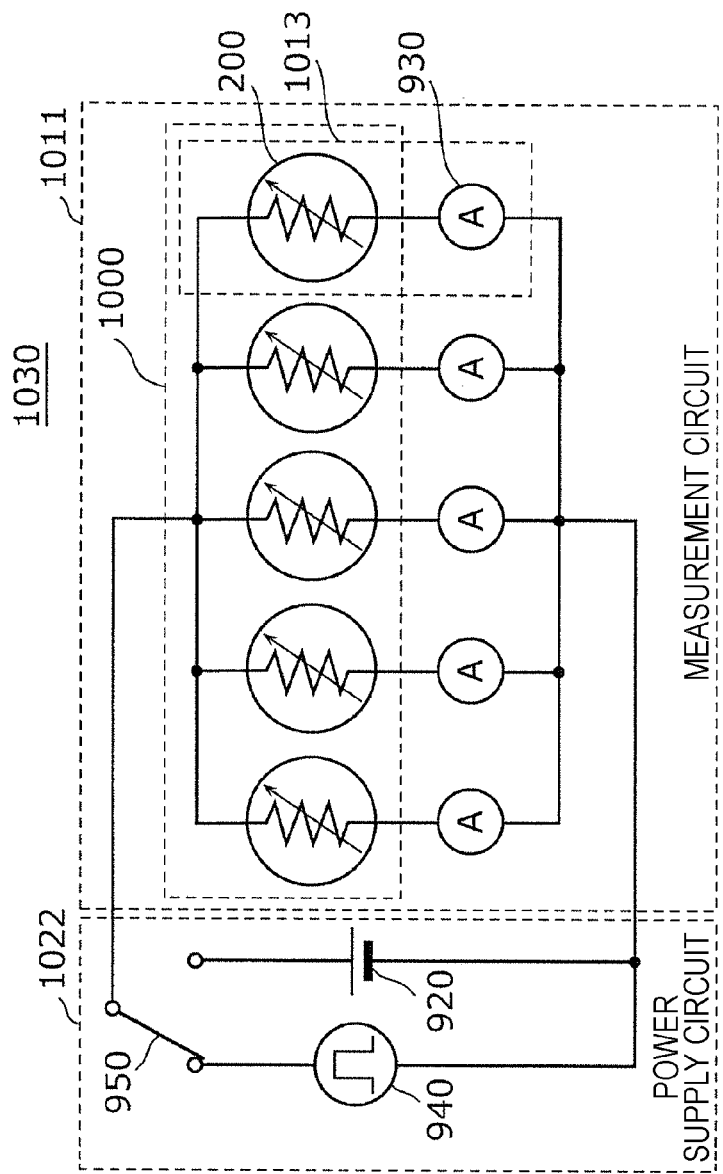
FIG. 12 is a circuit diagram illustrating an example of a gas detection circuit according to Third Embodiment.

FIG. 12 is a circuit diagram illustrating an example of a gas detection circuit according to Third Embodiment.

In the gas detection circuit 1030 shown in FIG. 12, the power supply circuit 1022 further includes a switch 950 and a reset power supply 940, compared to the gas detection circuit 1010 shown in FIG. 9.

In the gas detection circuit 1030, after detection of hydrogen-containing gas with the gas sensor 1000 and the current meters 930, the switch 950 is connected to the reset power supply 940. The reset power supply 940 applies a reset voltage to the gas detection devices 200 to electrically reset the gas detection devices 200, which have been in low resistive states by the hydrogen-containing gas, to high resistive states.

Accordingly, it is possible to repeatedly detect hydrogen-containing gas by resetting each of the gas detection devices 200 in the low resistive state after the detection of hydrogen-containing gas to the high resistive state.

In this embodiment, the reset voltage is 1.5 V as an example. The reset voltage must be higher than the detection voltage (e.g., 0.6 V) that is applied at all times during the monitoring of hydrogen-containing gas.

Figure 13:
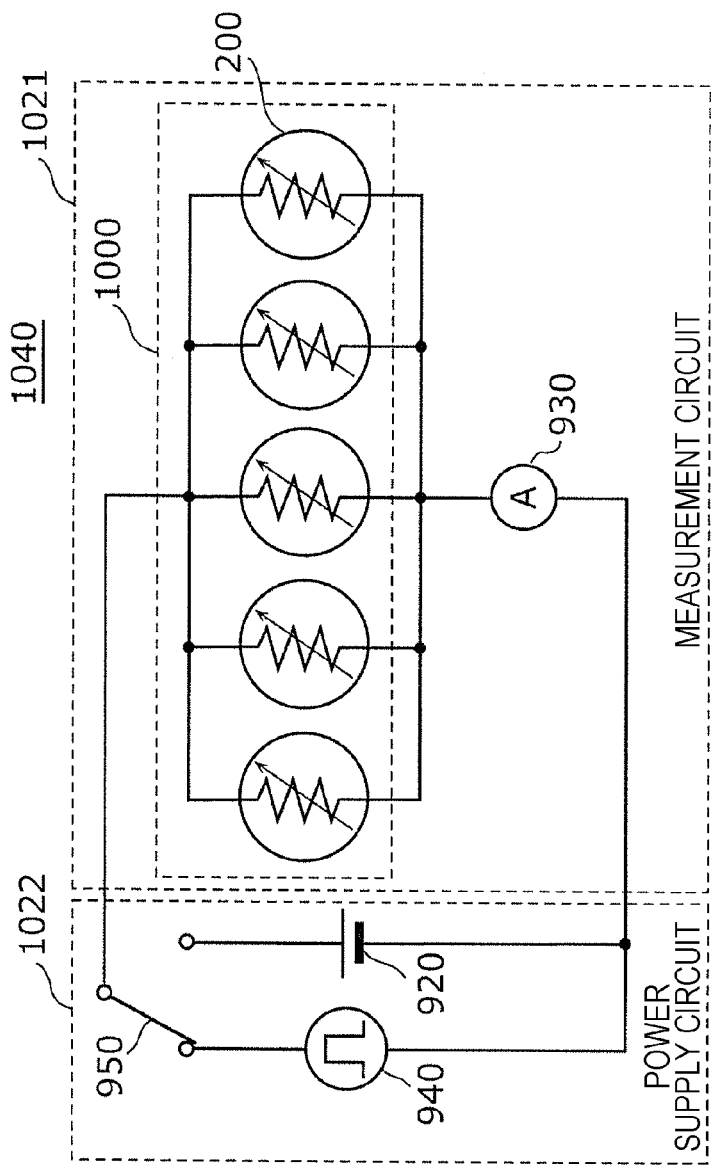
FIG. 13 is a circuit diagram illustrating an example of a gas detection circuit according to Third Embodiment.

FIG. 13 is a circuit diagram illustrating an example of a gas detection circuit according to Third Embodiment.

In the gas detection circuit 1040 shown in FIG. 13, the power supply circuit 1022 further includes a switch 950 and a reset power supply 940, compared to the gas detection circuit 1020 shown in FIG. 11.

The gas detection circuit 1040 also can repeatedly detect hydrogen-containing gas by resetting the gas detection devices 200 in the low resistive states after detection of hydrogen-containing gas to the high resistive states, as in the gas detection circuit 1020.

[Supplement]

In FIG. 12, the detection power supply 920 is an example of the "first power supply circuit" in the present disclosure, and the reset power supply 940 is an example of the "second power supply circuit" in the present disclosure. The "power supply circuit" in the present disclosure, for example, may be a power supply itself or may be a conversion circuit for converting the voltage of an external power supply to a desired voltage.

Overviews of Embodiments

A gas sensor according to an aspect includes a plurality of gas detection devices each including first and second electrodes disposed such that main surfaces thereof face each other; a metal oxide layer disposed so as to be in contact with the main surface of the first electrode and the main surface of the second electrode; a local area disposed in the inside of the metal oxide layer so as to be in contact with the second electrode and having a degree of oxygen deficiency higher than that of the metal oxide layer; and an insulation film covering the first electrode, the second electrode, and the metal oxide layer, wherein at least a part of the other surface opposite to the main surface of the second electrode is exposed without being covered with the insulation film. The gas detection devices have the same structure and the same shape and have characteristics of decreasing the resistance value between the first electrode and the second electrode by the contact of the second electrode with gas including gas molecules containing hydrogen atoms. The gas is detected through a reduction in the resistance value between the first electrode and the second electrode in each of a predetermined number of the plurality of gas detection devices.

In such a structure, the current flowing between the first electrode and the second electrode is concentrated in the local area having a high degree of oxygen deficiency. As a result, the temperature of the local area can be increased with a small amount of current.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area of the metal oxide layer to reduce the resistance value between the first electrode and the second electrode.

More specifically, an increase in the temperature of the local area increases the temperature of the surface of the second electrode. This increase in the temperature enhances the efficiency of releasing hydrogen atoms from hydrogen molecules at the second electrode by the catalytic action of the second electrode.

The contact of hydrogen molecules passed through the insulation film with the second electrode releases hydrogen atoms from the hydrogen molecules. The released hydrogen atoms diffuse in the second electrode and reach the local area. The hydrogen atoms then bind to oxygen of the metal oxide present in the local area into water ($H_2O$). Consequently, the degree of oxygen deficiency of the local area is further increased. As a result, current easily flows in the local area, and the resistance between the first electrode and the second electrode decreases.

Consequently, the resulting gas sensor can detect hydrogen-containing gas utilizing the self-heating and gas sensitivity of the local area formed in the inside of the metal oxide layer without heating with a heater and thus has excellent power-saving properties.

The reaction time for decreasing the resistance value between the first electrode and the second electrode depending on hydrogen-containing gas varies in each gas detection device and in each detection behavior of hydrogen-containing gas according to a certain distribution. Accordingly, the gas sensor detects hydrogen-containing gas through a reduction in the resistance value in each of a predetermined number of the plurality of gas detection devices. That is, the detection of hydrogen-containing gas is performed by a predetermined number of gas detection devices showing a reduction in the resistance value earlier in the distribution (e.g., by the gas detection device decreased the resistance value at the earliest time). Consequently, the resulting gas sensor can stably detect hydrogen-containing gas with high sensitivity by utilizing the variation in the reaction time.

In each of the gas detection devices, the metal oxide layer is a laminate composed of a first metal oxide layer made of a first metal oxide and a second metal oxide layer made of a second metal oxide having a degree of oxygen deficiency less than that of the first metal oxide. The first metal oxide layer is in contact with the first electrode, and the second metal oxide layer is in contact with the second electrode. The local area is formed so as to at least pass through the second metal oxide layer and be in contact with the second electrode and may have a degree of oxygen deficiency higher than that of the second metal oxide layer.

In such a structure, the employment of the layered structure having excellent resistance change characteristics as the metal oxide layer can provide a gas sensor having excellent characteristics of detecting hydrogen-containing gas.

In each of the gas detection devices, the second electrode may be made of a material having a catalytic action for releasing hydrogen atoms from the gas molecules.

In such a structure, hydrogen atoms are released from the hydrogen molecules in the portion of the second electrode being in contact with the local area. The released hydrogen atoms bind to oxygen atoms in the local area of the metal oxide layer to reduce the resistance value between the first electrode and the second electrode.

In each of the gas detection devices, the second electrode may be made of platinum, palladium, iridium, or an alloy containing at least one of platinum, palladium, and iridium.

In such a structure, the second electrode can release hydrogen atoms from the hydrogen molecules by the catalytic action of platinum or palladium.

The gas sensor may include a measurement circuit including a plurality of series circuits that are each composed of a current meter and a gas detection device connected to each other in series and are connected in parallel to one another, where the current meters may measure the current flowing in the respective gas detection devices connected to the corresponding current meters when a detection voltage is applied between the first electrode and the second electrode of each of the gas detection devices.

Such a structure can detect the hydrogen-containing gas through an increase in the current measured with the current meter included in the series circuit.

The gas sensor may include a measurement circuit including a parallel circuit composed of the gas detection devices connected in parallel to one another and a current meter connected in series to the parallel circuit, wherein the current meter may measure the current flowing in the parallel circuit when a detection voltage is applied between the first electrode and the second electrode of each of the gas detection devices.

In such a structure, the hydrogen-containing gas can be detected through an increase in the current measured by the current meter in an amount corresponding to the reduction of the resistance value in each of a predetermined number of the plurality of f gas detection devices.

In each of the gas detection devices, the metal oxide layer may reversibly transition between a high resistive state and a low resistive state having a resistance value less than that of the high resistive state based on the voltage applied between the first electrode and the second electrode.

In such a structure, transition of the resistive state of the metal oxide layer can be electrically performed, in addition to the transition by hydrogen-containing gas. For example, the gas as an object to be tested may be brought into contact with the metal oxide layer after electrically setting the metal oxide layer to a high resistive state. In such a case, a reduction in the resistance value can be clearly detected to enhance the characteristics of detecting hydrogen-containing gas.

Each of the gas detection devices may be set to a high resistive state before detection of the gas by applying a reset voltage between the first electrode and the second electrode.

In such a structure, since a reduction in the resistance value of the gas detection device electrically set to a high resistive state is detected, the reduction in the resistance value can be clearly detected to enhance the characteristics of detecting hydrogen-containing gas.

Each of the gas detection devices may be set to a high resistive state after detection of the gas by applying a reset voltage between the first electrode and the second electrode.

In such a structure, even if the gas detection devices are maintained at low resistive states after the detection of hydrogen-containing gas, it is possible to detect hydrogen-containing gas again by electrical reset to high resistive states.

The gas sensor may include a power supply circuit including a detection power supply generating a detection voltage for measuring current flowing in the plurality of gas detection devices, a reset power supply generating a reset voltage for setting the gas detection devices to high resistive states, and a changeover switch for switching the detection power supply and the reset power supply to selectively applying any one of the detection voltage and the reset voltage between the first electrode and the second electrode of each of the gas detection devices.

In such a structure, the gas sensor can have high convenience as a module component including power supplies for current measurement and giving high resistance (reset).

The absolute value of the detection voltage may be less than that of the reset voltage.

In such a structure, the gas sensor can have excellent power-saving properties by applying minimum voltages suitable for current measurement and giving high resistance (reset) to the gas detection devices.

The power supply circuit may apply a voltage, for activating the characteristics of reducing the resistance value between the first electrode and the second electrode by the contact of the second electrode with gas including gas molecules containing hydrogen atoms, at all times between the first electrode and the second electrode.

In such a structure, it is possible to continuously monitor leakage of hydrogen-containing gas with a slight power by utilizing the power-saving properties of the gas sensor.

The metal oxide layer in each of the gas detection devices may be made of a transition metal oxide or an aluminum oxide.

In such a structure, the gas sensor can have excellent characteristics of detecting hydrogen-containing gas by using a transition metal oxide or an aluminum oxide having excellent resistance change characteristics as each of the first metal oxide and the second metal oxide.

In each of the gas detection devices, the transition metal oxide may be any of tantalum oxide, hafnium oxide, and zirconium oxide.

In such a structure, the gas sensor can have excellent characteristics of detecting hydrogen-containing gas by using tantalum oxide, hafnium oxide, or zirconium oxide having excellent resistance change characteristics as the transition metal oxide.

In each of the gas detection devices, the local area generates heat by the current flowing between the first electrode and the second electrode; hydrogen atoms are thereby released from the gas molecules in the portion of the second electrode being in contact with the local area; and the released hydrogen atoms bind to oxygen atoms in the local area of the metal oxide layer. The resistance value between the first electrode and the second electrode may be thus reduced.

In such a structure, the current flowing between the first electrode and the second electrode is concentrated in the local area having a high degree of oxygen deficiency. As a result, the temperature of the local area can be increased with a small amount of current.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area of the metal oxide layer to reduce the resistance value between the first electrode and the second electrode.

More specifically, an increase in the temperature of the local area increases the temperature of the surface of the second electrode. This increase in the temperature enhances the efficiency of releasing hydrogen atoms from gas molecules containing hydrogen atoms at the second electrode by the catalytic action of the second electrode.

The contact of gas molecules containing hydrogen atoms passed through the insulation film with the second electrode releases hydrogen atoms from the gas molecules. The released hydrogen atoms diffuse in the second electrode and reach the local area. The hydrogen atoms then bind to oxygen of the metal oxide present in the local area into water. Consequently, the degree of oxygen deficiency of the local area is further increased. As a result, current easily flows in the local area, and the resistance between the first electrode and the second electrode decreases.

Consequently, the resulting gas sensor can detect hydrogen-containing gas utilizing the self-heating and gas sensitivity of the local area formed in the inside of the metal oxide layer without heating with a heater and thus has excellent power-saving properties.

The method of detecting hydrogen according to an aspect uses a gas sensor including a plurality of gas detection devices. The gas detection devices each include first and second electrodes disposed such that main surfaces thereof face each other and a metal oxide layer disposed so as to be in contact with the main surface of the first electrode and the main surface of the second electrode and have the same structure and the same size. The method includes bringing gas including gas molecules containing hydrogen atoms into contact with the second electrodes of the gas detection devices and detecting the gas through a reduction in the resistance value between the first electrode and the second electrode in a predetermined number of the plurality of gas detection devices.

In such a method, hydrogen can be detected with excellent power-saving properties with the gas sensor generating heat by only the current for detecting the resistive state and detecting hydrogen-containing gas without heating with a separate heater.

The gas-detecting apparatus according to the present disclosure is useful for, for example, fuel-cell vehicles, hydrogen stations, and hydrogen plants.

What is claimed is:

1. A gas-detecting apparatus comprising:
a measurement circuit including
a gas sensor that includes an insulation film and detection cells covered with the insulation an insulation film, and
at least one measurement instrument that monitors resistance values of the detection cells; and
a decision circuit that decides whether gas containing hydrogen atoms is detected or not based on at least one change in the resistance values, wherein:
each of the detection cells includes:
a first electrode;
a second electrode having a surface exposed from the insulation film; and
a metal oxide layer disposed between the first electrode and the second electrode, the metal oxide layer including a bulk area and a local area penetrating into the bulk area, a side face of the local area being surrounded by the bulk area,
a degree of oxygen deficiency of the local area is higher than that of the bulk area,
an upper surface of the local area and an upper surface of the bulk area are in direct contact with a bottom surface of the second electrode,
a bottom of the local area is away from an upper surface of the first electrode, and
the resistance values of the detection cells are each allowed to decrease by a contact of the gas with the second electrode.

2. The gas-detecting apparatus according to claim 1, wherein
the detection cells have the same size and the same structure.

3. The gas-detecting apparatus according to claim 1, wherein
the detection cells are N detection cells, where N is an integer of two or more; and
the decision circuit decides that the gas is detected when M of the resistance values of the N detection cells are decreased, where M is predetermined to be an integer of one or more and less than N.

4. The gas-detecting apparatus according to claim 3, wherein
the M is predetermined to be an integer of two or more.

5. The gas-detecting apparatus according to claim 1, wherein
the at least one measurement instrument are a plurality of measurement instruments that concurrently monitor respective resistance values of the detection cells.

6. The gas-detecting apparatus according to claim 5, wherein
the plurality of measurement instruments are a plurality of current meters, each of which monitors a current value flowing in a corresponding one of the detection cells, the plurality of current meters being respectively connected in series to the detection cells.

7. The gas-detecting apparatus according to claim 6, further comprising:
a power supply circuit that applies a voltage to the measurement circuit to allow current to flow in each of the detection cells.

8. The gas-detecting apparatus according to claim 1, wherein
the at least one measurement instrument is a single measurement instrument that monitors a combined resistance value of the detection cells.

9. The gas-detecting apparatus according to claim 8, wherein
the detection cells are connected in parallel to one another.

10. The gas-detecting apparatus according to claim 8, wherein
the single measurement instrument is a single current meter that monitors a combined current value flowing in the detection cells.

11. The gas-detecting apparatus according to claim 10, further comprising:
a power supply circuit that applies a voltage to the measurement circuit to allow current to flow in each of the detection cells.

12. The gas-detecting apparatus according to claim 1, wherein
the exposed surface of the second electrode is allowed to come in contact with the gas.

13. The gas-detecting apparatus according to claim 1, wherein
each of the detection cells reversibly transitions between a high resistive state and a low resistive state in response to a voltage applied between the first electrode and the second electrode, a resistance value in the high resistive state being higher than that in the low resistive state.

14. The gas-detecting apparatus according to claim 13, further comprising:
a power supply circuit that, before the at least one measurement instrument monitors the resistance values of the detection cells, applies the voltage to the measurement circuit to set each of the detection cells to the high resistive state.

15. The gas-detecting apparatus according to claim 13, further comprising:
a power supply circuit that, after the decision circuit decides that the gas is detected, applies the voltage to the measurement circuit to set each of the detection cells to the high resistive state.

16. A method of detecting gas with a gas sensor,
the gas sensor comprising:
an insulation film, and
detection cells covered with the insulation film, wherein
each of the detection cells includes:
a first electrode;
a second electrode having a surface exposed from the insulation film; and
a metal oxide layer disposed between the first electrode and the second electrode, the mental oxide layer including a bulk area and a local area penetrating into the bulk area, a side face of the local area being surrounded by the bulk area, a degree of oxygen deficiency of the local area being higher than that of the bulk area, an upper surface of the local area and an upper surface of the bulk area being in direct contact with a bottom surface of the second electrode, a bottom of the local area being away from an upper surface of the first electrode, and
the method of detecting gas comprising:
monitoring resistance values of the detection cells; and
deciding whether gas containing hydrogen atoms is detected or not based on at least one change in the resistance values.

17. The method of detecting gas according to claim 16, wherein
the detection cells are N detection cells, where N is an integer of two or more; and
in the deciding, detection of the gas is decided when M of the resistance values of the N detection cells are decreased, where M is predetermined to be an integer of one or more and less than N.

18. The method of detecting gas according to claim 16, wherein
in the monitoring, the resistance values of the detection cells are concurrently monitored.

19. The method of detecting gas according to claim 16, wherein
in the monitoring, a combined resistance value of the detection cells is monitored.

20. A gas-detecting apparatus comprising:
a measurement circuit including
a gas sensor that includes an insulation film and detection cells covered with the insulation an insulation film, and
at least one measurement instrument that monitors resistance values of the detection cells; and
a decision circuit that decides whether gas containing hydrogen atoms is detected or not based on at least one change in the resistance values, wherein:
the detection cells each include
a first electrode,
a second electrode having a surface exposed from the insulation film, and
a first metal oxide layer, a bottom surface of the first metal oxide layer being in direct contact with an upper surface of the first electrode,
a second metal oxide layer, an upper surface layer of the second metal oxide layer being in direct contact with a bottom surface of the second electrode, and
a local area passing through the second metal oxide layer, an upper surface of the local area being in direct contact with the bottom surface of the second electrode, a bottom of the local area being away from the upper surface of the first electrode;
a degree of oxygen deficiency of the first metal oxide layer is higher than that of the second metal oxide layer;
a degree of oxygen deficiency of the local area is higher than that of the second metal oxide layer; and
the resistance values of the detection cells are each allowed to decrease by a contact of the gas with the second electrode.

* * * * *